US012704443B2

(12) United States Patent
Takemori et al.

(10) Patent No.: US 12,704,443 B2
(45) Date of Patent: Aug. 11, 2026

(54) COMPOUND, CELLULAR VESICLE STAINING AGENT, AND METHOD OF FLUORESCENT STAINING FOR CELLULAR VESICLES

(71) Applicant: National University Corporation Tokai National Higher Education and Research System, Nagoya (JP)

(72) Inventors: Hiroshi Takemori, Gifu (JP); Kyoji Furuta, Gifu (JP); Yoko Morita, Gifu (JP)

(73) Assignee: National University Corporation Tokai National Higher Education and Research System, Nagoya (JP)

( * ) Notice: Subject to any disclaimer, the term of this patent is extended or adjusted under 35 U.S.C. 154(b) by 486 days.

(21) Appl. No.: 18/263,523

(22) PCT Filed: Jan. 19, 2022

(86) PCT No.: PCT/JP2022/001692
§ 371 (c)(1),
(2) Date: Jul. 28, 2023

(87) PCT Pub. No.: WO2022/163446
PCT Pub. Date: Aug. 4, 2022

(65) Prior Publication Data

US 2024/0125678 A1 Apr. 18, 2024

(30) Foreign Application Priority Data

Jan. 28, 2021 (JP) ................................ 2021-012443

(51) Int. Cl.
*G01N 1/30* (2006.01)
*C07C 217/10* (2006.01)
(Continued)

(52) U.S. Cl.
CPC ............ *G01N 1/30* (2013.01); *C07C 217/10* (2013.01); *C07C 217/74* (2013.01); *C07D 271/12* (2013.01); *G01N 2001/302* (2013.01)

(58) Field of Classification Search
CPC .. G01N 1/30; G01N 2001/302; C07C 217/10; C07C 217/74; C07D 271/12
(Continued)

(56) References Cited

U.S. PATENT DOCUMENTS

2002/0166181 A1 11/2002 Chassot et al.
2014/0010762 A1 1/2014 Charlton et al.
(Continued)

FOREIGN PATENT DOCUMENTS

CN 110862340 A 3/2020
JP 2005-249391 A 9/2005
(Continued)

OTHER PUBLICATIONS

Extended European Search Report issued by EPO dated Dec. 5, 2024 for corresponding European Application No. 22745669.6 (7 pages).

(Continued)

*Primary Examiner* — Anita Nassiri-Motlagh
(74) *Attorney, Agent, or Firm* — INTELLECTUAL PROPERTY LAW GROUP LLP

(57) ABSTRACT

An object is to provide a novel compound that specifically conjugates with intracellular and/or extracellular vesicles, a cellular vesicle staining agent, and a method of fluorescent staining for cellular vesicles. The object can be achieved by a compound expressed by the following Formula (1).

[Formula 1]

(Continued)

(1)

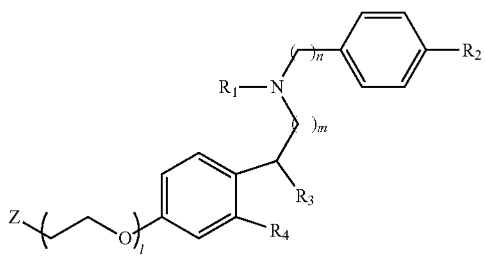

(In Formula (1), $R_1$ represents H, a $C_1$-$C_6$ alkyl group, a hydroxy group, an amino group, or a carboxy group. $R_2$ represents H, a $C_1$-$C_{18}$ alkyl group, a $C_1$-$C_{18}$ alkoxy group, a halogen element, $NO_2$ or $N(CH_3)_2$. $R_3$ and $R_4$ each independently represent H or $CH_3$, where $R_3$ and $R_4$ may be bonded to each other to form a ring, and in such a case, $R_3$ and $R_4$ are $CH_2$. Herein, 1 represents 1 or 2, m represents 0 or 1, n represents 1, 2, or 3, and Z represents a fluorescent group).

20 Claims, 8 Drawing Sheets

(51) Int. Cl.
*C07C 217/74* (2006.01)
*C07D 271/12* (2006.01)

(58) Field of Classification Search
USPC .................................................... 252/301.16
See application file for complete search history.

(56) References Cited

U.S. PATENT DOCUMENTS

2014/0248654 A1 9/2014 Urano et al.
2022/0145376 A1 5/2022 Watanabe et al.

FOREIGN PATENT DOCUMENTS

JP 2020-204604 A 12/2020
WO WO 2013/035767 A1 3/2013
WO WO 2020/235424 A1 11/2020
WO WO 2020/262374 A1 12/2020

OTHER PUBLICATIONS

China Office Action issued by CNIPA, dated Dec. 6, 2024 for corresponding China Patent Application No. 202280012040.0 with English machine translation (10 pages).
International Search Report, dated Mar. 22, 2022 for corresponding International Application No. PCT/JP2022/001692 with English translation (5 pages).
Written Opinion of the ISA, dated Mar. 22, 2022 for corresponding International Application No. PCT/JP2022/001692 with English translation (4 pages).
He, Lipeng et al., "Fluorescene responsive conjugated poly (tetraphenylethene) and its morphological transition from micelle to vesicle", Chemical Communications, 2015, 51(33), 7148-7151 (4 pages).

FIG.1A
FIG.1B
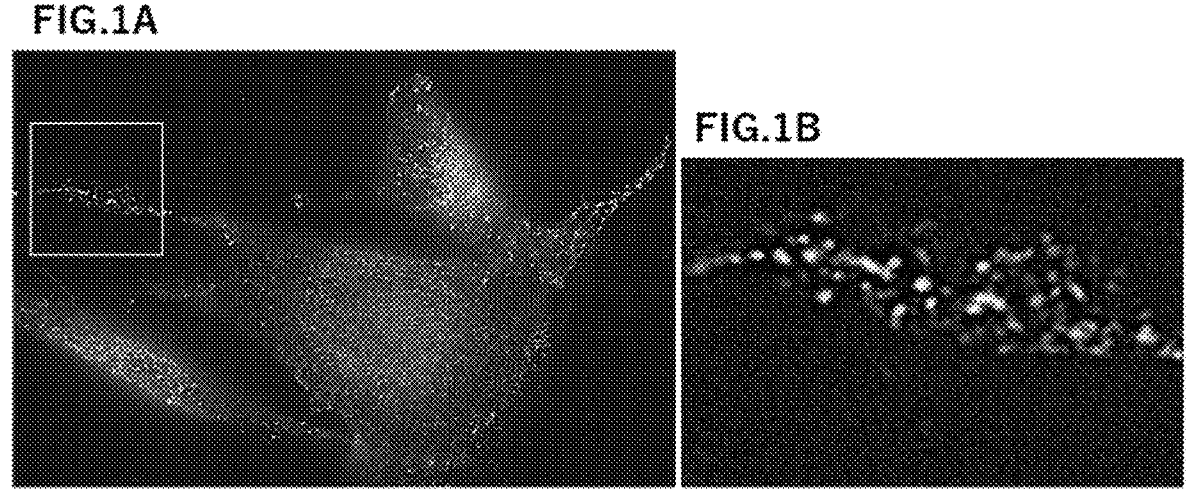
FIG.2A
FIG.2C
FIG.2E
FIG.2B
FIG.2D
FIG.2F
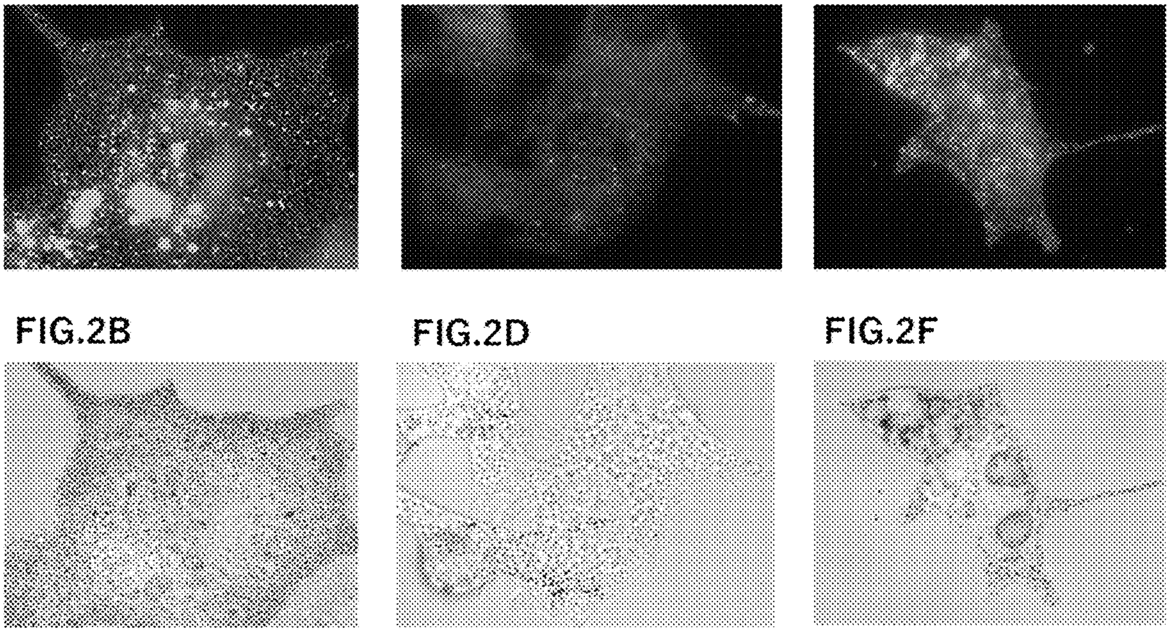

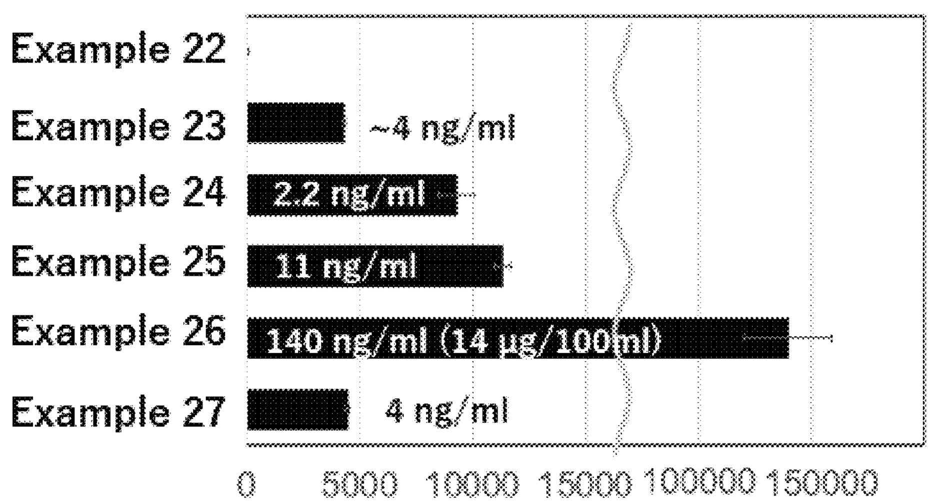
FIG. 9
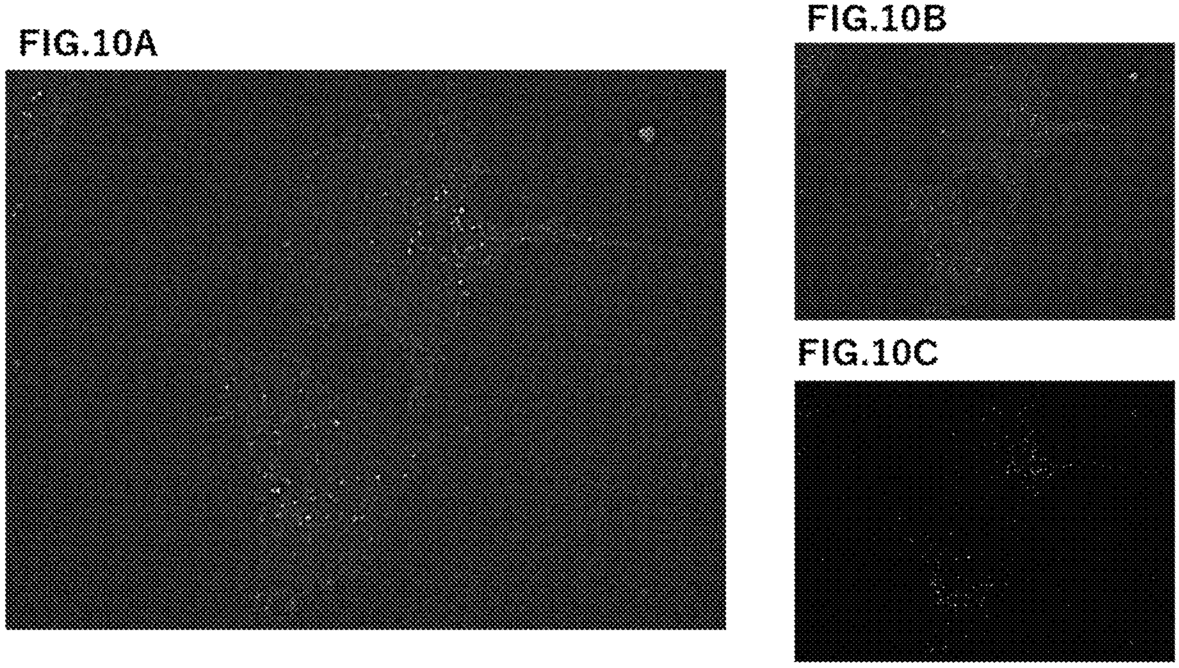
FIG.10A
FIG.10B
FIG.10C

COMPOUND, CELLULAR VESICLE STAINING AGENT, AND METHOD OF FLUORESCENT STAINING FOR CELLULAR VESICLES

CROSS-REFERENCE TO RELATED APPLICATIONS

This application is a U.S. National Phase application, under 35 U.S.C. § 371, of International Application no. PCT/JP2022/001692, with an international filing date of Jan. 19, 2022, and claims priority to Japanese application no. 2021-012443 filed on Jan. 28, 2021, each of which is hereby incorporated by reference for all purposes.

TECHNICAL FIELD

The disclosure of the present application relates to a compound, a cellular vesicle staining agent, and a method of fluorescent staining for cellular vesicles.

BACKGROUND ART

In recent years, endocytosis, a mechanism to incorporate extracellular molecules into cells, is known to be involved in cellular physiological functions and diseases, and many studies have been made. Indents on cellular surface caused by endocytosis move into cells and form endosomes. Thus, extracellular substances into incorporated cells by endocytosis are accumulated in the endosomes. Further, the endosomes determine destinations of the extracellularly incorporated molecules.

In addition, exosomes, vesicles secreted extracellularly, are formed in the endosomes originated from endocytosis. Since the exosomes contain cellular membrane components on their surface or inside, exosomes possess features that are originated from origins of the cells and thus play an important role in intercellular signaling. Furthermore, exosomes are released extracellularly, also exist in body fluids (blood, spinal fluid, urine, or the like) and circulate in bodies. It is thus expected that exosomes are used as diagnosis markers for diseases, etc. Further, melanosomes are known as endosome-derived vesicles as with exosomes. Melanosomes are produced in and released from melanocytes and transported and incorporated into keratinocytes. Evaluations of pharmaceutical products, cosmetics, or other products are performed basing on the mechanism for by measuring accumulation of melanosomes in keratinocytes.

Thus, detection and analysis of intracellular vesicles or extracellularly released vesicles that are derived from endosomes are important in understanding mechanisms by which cells incorporate and release external substances. Patent Literature 1 discloses the analysis of exosomes derived from a variety of abnormal cells. Further, Patent Literature 2 discloses a method of co-culturing fluorescently labeled keratinocytes and unlabeled melanocytes, by a method with a fluorescently labeled melanosome-specific antibody, which is analyzed by a flow cytometer.

CITATION LIST

Patent Literature

Patent Literature 1: Japanese Patent Application Laid-Open No. 2020-204604

Patent Literature 2: Japanese Patent Application Laid-Open No. 2005-249391

SUMMARY OF INVENTION

Technical Problem

Patent Literature 1 and Patent Literature 2 disclose the detection of vesicles through fluorescent labeling using fluorescent dyes. Fluorescent labeling is a simple method that only requires mixing vesicles with fluorescent dyes after their collection, and it is widely used. However, there are issues with sample loss caused by the operation of removing unreacted fluorescent dyes after fluorescent labeling, as well as the formation of micelles due to coagulation between the fluorescent dyes. Therefore, there is a demand for a novel compound that can be used as a staining agent specifically for selectively staining vesicles.

Accordingly, the disclosure in the present application has an object to provide a novel compound that specifically conjugates with intracellular and/or extracellular vesicles, a cellular vesicle staining agent, and a method of fluorescent staining for cellular vesicles. Other optional and additional advantageous effects of the disclosure in the present application will be revealed in embodiments for implementing the invention.

Solution to Problem

[1] A compound expressed by following Formula (1):

[Formula 1]

(1)

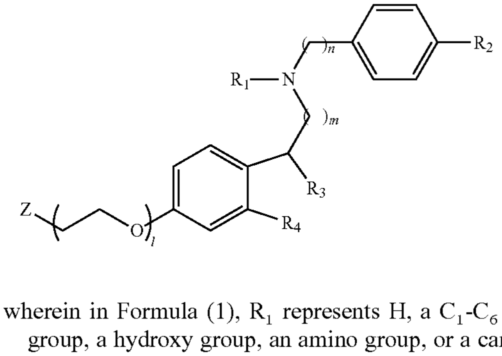

wherein in Formula (1), $R_1$ represents H, a $C_1$-$C_6$ alkyl group, a hydroxy group, an amino group, or a carboxy group, $R_2$ represents H, a $C_1$-$C_{18}$ alkyl group, a $C_1$-$C_{18}$ alkoxy group, a halogen element, $NO_2$ or $N(CH_3)_2$, and $R_3$ and $R_4$ each independently represent H or $CH_3$, where $R_3$ and $R_4$ may be bonded to each other to form a ring and, when $R_3$ and $R_4$ are bonded to each other to form a ring, $R_3$ and $R_4$ are $CH_2$, and wherein 1 represents 1 or 2, m represents 0 or 1, n represents 1, 2, or 3, and Z represents a fluorescent group.

[2] The compound according to [1] above, wherein the compound expressed by Formula (1) is a compound expressed by following Formula (2):

[Formula 2]

(2)

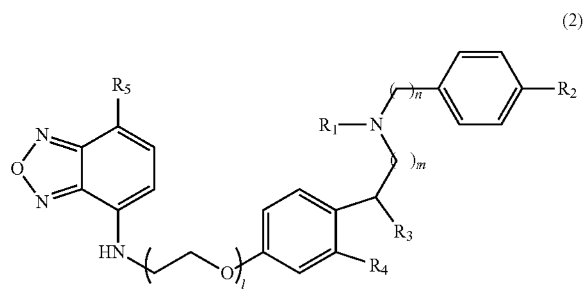

wherein in Formula (2), $R_1$ represents H or $CH_3$, $R_2$ represents H, $CH_3$, $OCH_3$, or $N(CH_3)_2$, $R_3$ and $R_4$ each independently represent H or $CH_3$, where $R_3$ and $R_4$ may be bonded to each other to form a ring and, when $R_3$ and $R_4$ are bonded to each other to form a ring, $R_3$ and $R_4$ are $CH_2$, and $R_5$ represents $NO_2$, $SO_2NH_2$, or $SO_2N(CH_3)_2$, and wherein 1 represents 1 or 2, m represents 0 or 1, and n represents 1, 2, or 3.

[3] The compound according to [1] above, wherein the compound expressed by Formula (1) is a compound expressed by following Formula (3):

[Formula 3]

(3)

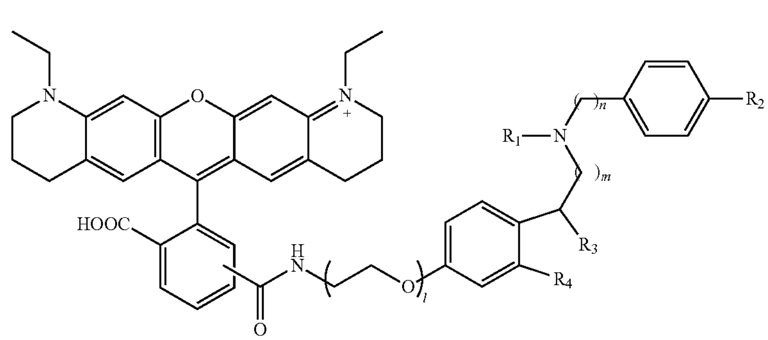

wherein in Formula (3), $R_1$ represents H or $CH_3$, $R_2$ represents H, $CH_3$, $OCH_3$, or $N(CH_3)_2$, and $R_3$ and $R_4$ each independently represent H or $CH_3$, where $R_3$ and $R_4$ may be bonded to each other to form a ring, and when $R_3$ and $R_4$ are bonded to each other to form a ring, $R_3$ and $R_4$ are $CH_2$, and wherein 1 represents 1 or 2, m represents 0 or 1, and n represents 1, 2, or 3.

[4] A cellular vesicle staining agent comprising the compound according to any one of [1] to [3] above.

[5] The cellular vesicle staining agent according to [4] above further comprising another fluorescent compound.

[6] A method of fluorescent staining for cellular vesicles, the method comprising:

a staining step of selecting any one of the compound according to [1] to [3] above or the cellular vesicle staining agent according to [4] and [5] above and staining cellular vesicles by using the selected one; and a detection step of detecting stained cellular vesicles in a sample.

[7] The method of fluorescent staining for cellular vesicles according to [6] above further comprising an evaluation step of evaluating the sample after the detection step.

[8] The method of fluorescent staining for cellular vesicles according to [7] above, wherein the sample includes cosmetics, and wherein the method measures the cellular vesicle incorporated in a cell to evaluate the cosmetics.

[9] The method of fluorescent staining for cellular vesicles according to [7] above, wherein the sample includes pharmaceutical products, and wherein the method measures the cellular vesicles incorporated in cells to evaluate the pharmaceutical product.

[10] The method of fluorescent staining for cellular vesicles according to [7] above, wherein the sample includes cells, and wherein the method measures the cellular vesicles in the cells to evaluate differentiation and quality of the cells.

[11] The method of fluorescent staining for cellular vesicles according to [7] above, wherein the sample includes foods, and wherein the method measures the cellular vesicles in the foods to evaluate the foods.

[12] The method of fluorescent staining for cellular vesicles according to [7] above, wherein the sample includes tissues collected from organisms, and wherein the method measures the cellular vesicles in the collected tissues to evaluate the tissues.

Advantageous Effect

Since there is no need for operation of removing unreacted dyes after labeling, sample loss can be suppressed.

BRIEF DESCRIPTION OF DRAWINGS

FIGS. 1A-1B represent photographs as substitutes for drawings illustrating a result of Example 13. FIG. 1A illustrates a fluorescence microscopic image of a whole cell. FIG. 1B illustrates an enlarged view of a part surrounded by the frame of FIG. 1A.

FIGS. 2A-2F represent photographs as substitutes for drawings illustrating a result of Example 14. FIG. 2A illustrates a fluorescence microscopic image of observed fluorescence emitted from Compound 1 before addition of a PIKfyve inhibitor. FIG. 2B illustrates a phase-contrast microscopic image before the addition of the PIKfyve inhibitor. FIG. 2C illustrates a fluorescence microscopic image of observed fluorescence emitted from Compound 1 after the addition of the PIKfyve inhibitor. FIG. 2D illustrates a phase-contrast microscopic image after the addition of the PIKfyve inhibitor. FIG. 2E represents a fluorescence microscopic image of observed fluorescence emitted from Compound 1 after cells were cultured for 3 hours after removal of the PIKfyve. FIG. 2F represents a phase-contrast microscopic image after the cells were cultured for 3 hours after the removal of the PIKfyve.

FIG. 3A illustrates a fluorescence microscopic image of Example 15. FIG. 3B illustrates a fluorescence microscopic image of Example 16.

FIG. 4A illustrates a fluorescence microscopic image of observed fluorescence emitted from Compound 1. FIG. 4B illustrates a fluorescence microscopic image of observed fluorescence emitted from a mitochondrial staining reagent. FIG. 4C illustrates a fluorescence microscopic image of observed fluorescence emitted from DAPI staining nuclei. FIG. 4D illustrates a phase-contrast microscopic image.

FIG. 5A represents overlapped fluorescence microscopic images of Example 18 and Comparative example 1. FIG. 5B represents a fluorescence microscopic image of Example 18. FIG. 5C represents a fluorescence microscopic image of Comparative example 1.

FIG. 6A illustrates a fluorescence microscopic image of Example 19. FIG. 6B illustrates a phase-contrast microscopic image of Example 19. FIG. 6C illustrates a fluorescence microscopic image of Comparative example 2. FIG. 6D represents a phase-contrast microscopic image of Comparative example 2.

FIG. 9 is a diagram illustrating a result of exosome measurement in foods.

FIGS. 10A-10C represent photographs as substitutes for drawings illustrating incorporation of labeled exosomes into cells. FIG. 10A illustrates overlapped fluorescence microscopic images of fluorescence emitted from both Compound 1 and ExoSparkler Mem Dye-Red. FIG. 10B illustrates a fluorescence microscopic image of observed fluorescence emitted from Compound 1. FIG. 10C illustrates a fluorescence microscopic image of observed fluorescence emitted from ExoSparkler Mem Dye-Red.

FIG. 11A illustrates fluorescence microscopic images of Example 29 and phase-contrast microscopic images of Comparative example 4. FIG. 11B illustrates a result of Example 29. FIG. 11C illustrates a result of Comparative example 4.

FIG. 12A illustrates a fluorescence microscopic image of Example 30. FIG. 12B illustrates a phase-contrast microscopic image of Example 30. FIG. 12C illustrates a fluorescence microscopic image of Example 31. FIG. 12D illustrates a fluorescence microscopic image of Example 32. FIG. 12E illustrates a fluorescence microscopic image of Example 33. FIG. 12F illustrates a fluorescence microscopic image of Example 34. FIG. 12G illustrates a fluorescence microscopic image of Example 35. FIG. 12H illustrates a fluorescence microscopic image of Example 36. FIG. 12I illustrates a fluorescence microscopic image of Example 37. FIG. 12J illustrates a fluorescence microscopic image of Example 38. FIG. 12K illustrates a fluorescence microscopic image of Example 39.

DETAILED DESCRIPTION OF EMBODIMENTS

Embodiment of Compound

Figure 3A:
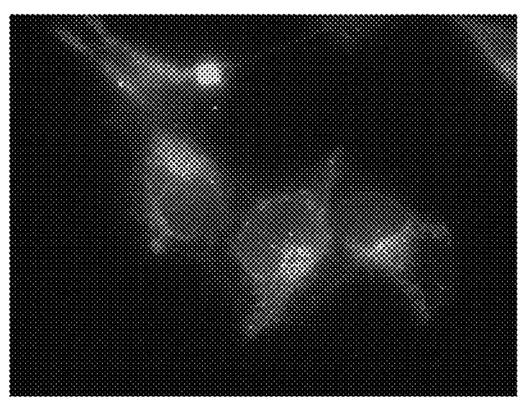
FIGS. 3A-3B represent photographs as substitutes for drawings illustrating a result of fluorescent staining of cellular vesicles of human cells by using Compound 1.

Compounds according to the embodiments will be described below.

The compounds according to the embodiments are characterized by being a compound expressed by the following Formula (1). Each compound expressed by Formula (1) specifically conjugates with cellular vesicles and thus emits fluorescence. The term "cellular vesicle" in this specification includes "intracellular vesicle" and "extracellular vesicle" such as exosomes.

[Formula 4]

(1)

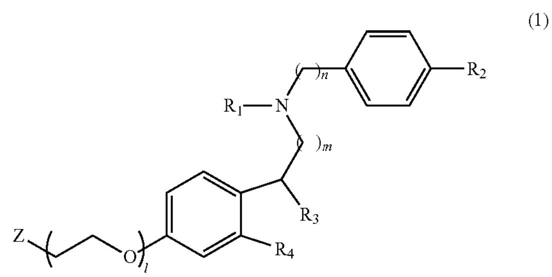

In Formula (1), $R_1$ represents H, a $C_1$-$C_6$ alkyl group, a hydroxy group, an amino group, or a carboxy group. The $C_1$-$C_6$ alkyl group may be linear, branched, or cyclic. For example, the $C_1$-$C_6$ alkyl group may be a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a neopentyl group, an n-hexyl group, an isohexyl group, a sec-hexyl group, a cyclopropyl group, a cyclobutyl group, a cyclopentyl group, a cyclohexyl group, or the like.

$R_2$ represents H, a $C_1$-$C_{18}$ alkyl group, a $C_1$-$C_{18}$ alkoxy group, a halogen element, $NO_2$, or $N(CH_3)_2$. The $C_1$-$C_{18}$ alkyl group may be linear, branched, or cyclic. The $C_1$-$C_{18}$ alkyl group may be, for example, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a neopentyl group, an n-hexyl group, an isohexyl group, a sec-hexyl group, an n-heptyl group, an isoheptyl group, a sec-heptyl group, an n-octyl group, an isooctyl group, a sec-octyl group, a nonyl group, a decyl group, an undecyl group, a dodecyl group, a tridecyl group, a tetradecyl group, a pentadecyl group, a hexadecyl group, a heptadecyl group, an octadecyl group, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group, a cyclooctadecyl group, or the like. The $C_1$-$C_{18}$ alkoxy group may be saturated or unsaturated and may have an aromatic ring. Further, the $C_1$-$C_{18}$ alkoxy group may be linear, branched, or cyclic. The $C_1$-$C_{18}$ alkoxy group may be, for example, a methoxy group, an ethoxy group, a propoxy group, an isopropoxy group, a cyclopropoxy group, an n-butoxy group, an isobutoxy group, a tert-butoxy group, a pentyloxy group, a hexyloxy group, an octyloxy group, a nonaoxy group, a decaneoxy group, an undecaneoxy group, a dodecaneoxy group, a tridecaneoxy group, a tetradecaneoxy group, a pentadecaneoxy group, a hexadecaneoxy group, a heptadecaneoxy group, an octadecaneoxy group, a vinyloxy group, an allyloxy group, a 1-propenyloxy group, an isopropenyloxy group, a 1-butenyloxy group, a 2-butenyloxy group, a 3-butenyloxy group, a 1,3-butanedienyloxy group, a 1-pentenyloxy group, a 2-pentenyloxy group, a 3-pentenyloxy group, a 4-pentenyloxy group, a hexynyloxy group, a hexidinyloxy group, a heptinyloxy group, a heptidinyloxy group, an octinyloxy group, an octidinyloxy group, a noninyloxy group, a nonidinyloxy group, a decynyloxy group, a decidinyloxy group, an undecynyloxy group, an undecidinyloxy group, a dodecyloxy group, a dodecidinyloxy group a tridecynyloxy group, a tridecidinyloxy group, a tetradecynyloxy group, a tetradecidinyloxy group, a pentadecynyloxy group, a pentadecidinyloxy group, a hexadecynyloxy group, a hexadecidinyloxy group, a heptadecynyloxy group, a heptadecidinyloxy group an octadecynyloxy group, an octadecidinyloxy group, a phenoxy group, a naphthoxy group, an anthryloxy group, a methylphenoxy group, a dimethylphenoxy group, a trimethylphenoxy group, an ethylphenoxy group, a diethylphenoxy group, a triethylphenoxy group, a propylphenoxy group, a butylphenoxy group, a methylnaphthoxy group, a dimethylnaphthoxy group, a trimethylnaphthoxy group, a methylanthryloxy group, an ethylanthryloxy group, a benzyloxy group, a phenethyloxy group, a naphthyl methyloxy group, a fluorenyl methyloxy group, or the like. The halogen element may be, for example, fluorine, chlorine, bromine, iodine, or the like.

$R_3$ and $R_4$ each independently represent H or $CH_3$, and $R_3$ and $R_4$ may be the same as or different from each other. Note that, $R_3$ and $R_4$ may be bonded to each other to form a ring, and in such a case, $R_3$ and $R_4$ are $CH_2$.

Herein, 1 represents 1 or 2, m represents 0 or 1, and n represents 1, 2, or 3.

Z represents a fluorescent group. The fluorescent group of the compound expressed by Formula (1) is not particularly limited as long as the fluorescent group emits fluorescence. The fluorescent may group for be, example, NBD (nitrobenzofurazan), ABD (sulfamoylbenzofurazan), DBD (dimethylaminosulfonylbenzofurazan), dimethylaminobenzylidene rhodanine, FAM, FITC, ROX, TAMRA, Alexa Fluor(registered trademark) 405, Alexa Fluor 488, Alexa Fluor 546, Alexa Fluor 555, Alexa Fluor 594, Alexa Fluor 647, Alexa Fluor 700, AMCA, AMCA-X, APC (Allophycocyanin), APC-XL, ATTO 390, ATTO 465, ATTO 488, ATTO 490LS, ATTO 520, ATTO 532, ATTO Rho6G, ATTO 542, ATTO 550, ATTO 565, ATTO 590, ATTO 594, ATTO 633, ATTO 647N, ATTO 647, ATTO 655, ATTO 665, ATTO 680, ATTO 700, ATTO 740, C-PC (C-Phycocyanin), Cy2, Cy3, Cy3.5, Cy5, Cy5.5, DY-405, DY-415, DY-475XL, DY-480XL, DY-481XL, DY-485XL, DY-490, DY-495, DY-495-X5, DY-500XL, DY-505-X5, DY-510XL, DY-520XL, DY-521XL, DY-547, DY-548, DY-549, DY-554, DY-555, DY-556, DY-560, DY-590, DY-610, DY-615, DY-630, DY-631, DY-632, DY-633, DY-634, DY-635, DY-636, DY-647, DY-648, DY-649, DY-650, DY-651, DY-652, DY-675, DY-676, DY-677, DY-678, DY-680, DY-681, DY-682, DY-700, DY-701, DY-730, DY-731, DY-732, DY-734, DY-749, DY-750, DY-751, DY-752, DY-776, DY-777, DY-780, DY-781, DY-782, DyLight 405, DyLight 488, DyLight 547, DyLight 549, DyLight 594, DyLight 633, DyLight 647, DyLight 649, DyLight 680, DyLight 750, DyLight 800, ECD, Fluorescein, HiLyte Flour 488, HiLyte Fluor 555, HiLyte Fluor 647, HiLyte Fluor 680, HiLyte Fluor 750, HiLyte Fluor TR, HiLyte Plus 555, HiLyte Plus 647, HiLyte Plus 750, IRDye700DX, IRDye800, IRDye800CW, MFP488, MFP555, MFP590, MFP631, NorthernLights 493, NorthernLights 557, NorthernLights 637, Oyster 500, Oyster 550, Oyster 556, Oyster 645, Oyster 650, Oyster 656, Pacific Blue, PE (phycoerythrin), B-PE, R-PE, PerCP, Phycocyanin, PREX710, Quantum Red, Rhodamine, ROX (X-Rhodamine, Rhodamine Red X), Royal Blue, Spectrum Green, Spectrum Orange, Spectrum Red, Texas Red, Tri-Color, TRITC, or the like. Further, the fluorescent group Z may be bonded in any manner as long as the compound expressed by Formula (1) can fluorescence when having stained cellular vesicles.

More specific examples of the compound expressed by Formula (1) may be compounds expressed by Formula (2) and compounds expressed by Formula (3) below.

[Formula 5]

(2)

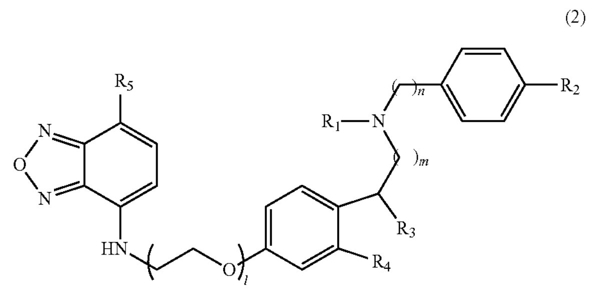

In Formula (2), $R_1$ represents H or $CH_3$. $R_2$ represents H, $CH_3$, $OCH_3$, or $N(CH_3)_2$. $R_3$ and $R_4$ each independently represent H or $CH_3$. Note that $R_3$ and $R_4$ may be bonded to each other to form a ring, and in such a case, $R_3$ and $R_4$ are $CH_2$. $R_5$ represents $NO_2$, $SO_2NH_2$, or $SO_2N(CH_3)_2$. Herein, 1 represents 1 or 2, m represents 0 or 1, and n represents 1, 2, or 3.

[Formula 6]

(3)

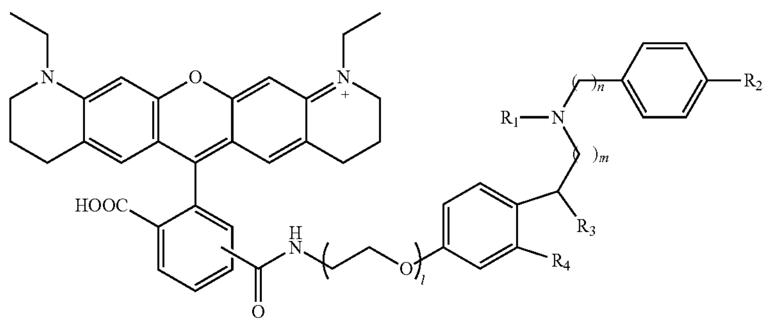

In Formula (3), $R_1$ represents H or $CH_3$. $R_2$ represents H, $CH_3$, $OCH_3$, or $N(CH_3)_2$. $R_3$ and $R_4$ each independently represent H or $CH_3$. Note that $R_3$ and $R_4$ may be bonded to each other to form a ring, and in such a case, $R_3$ and $R_4$ are $CH_2$. Herein, 1 represents 1 or 2, m represents 0 or 1, and n represents 1, 2, or 3.

Specific examples of the compound expressed by Formula (2) and the compound expressed by Formula (3) will be represented below but are not limited to these compounds illustrated as examples.

[Formula 7]

1

2

3

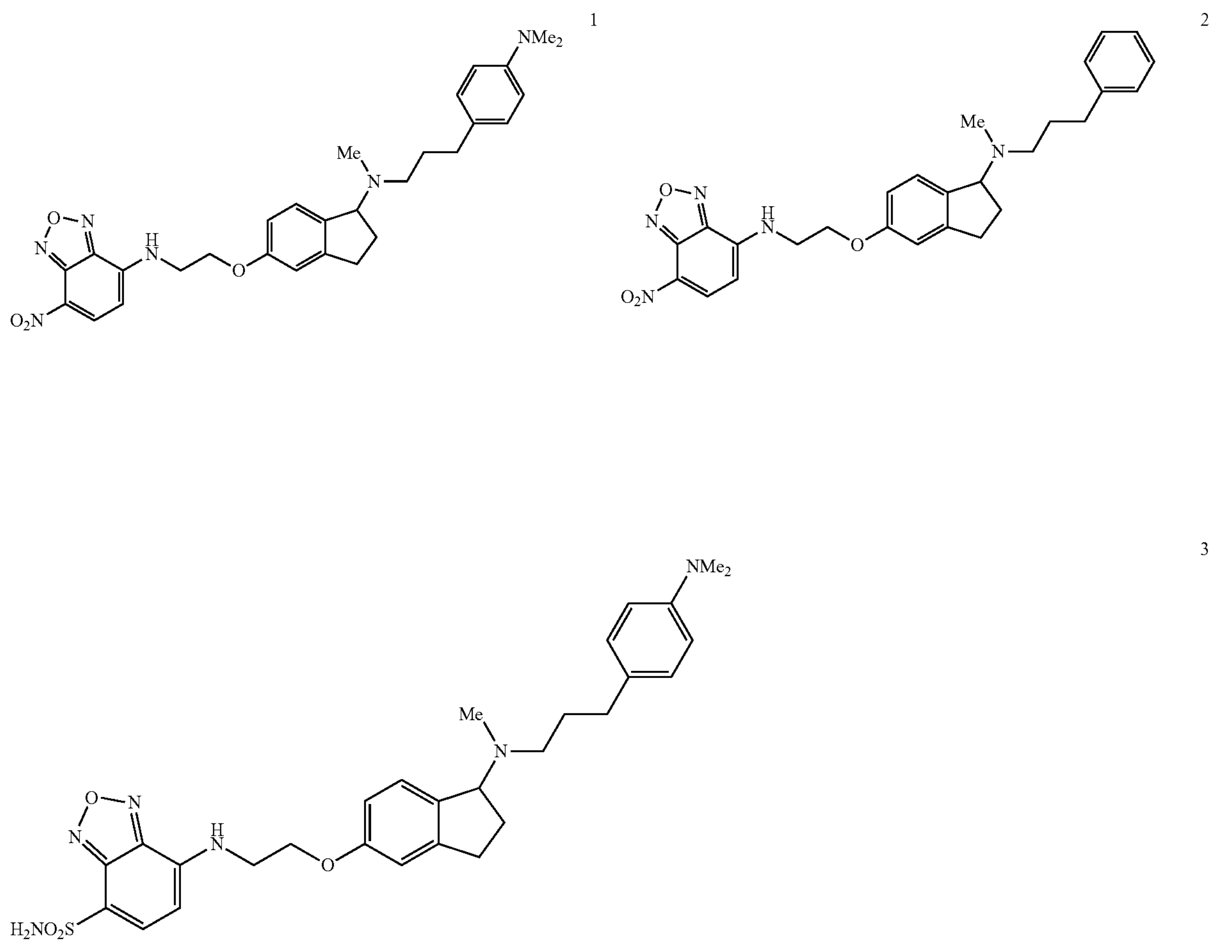

-continued
4
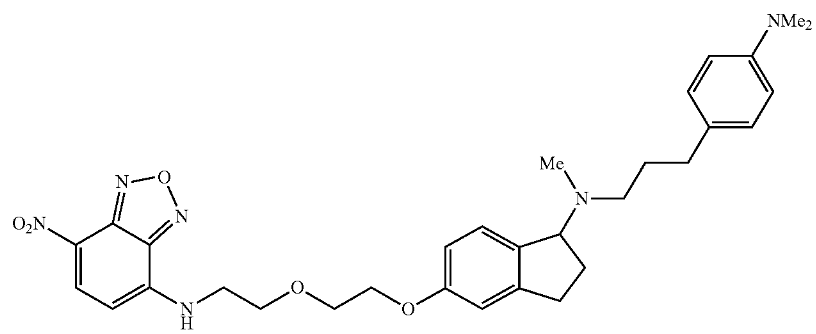
5
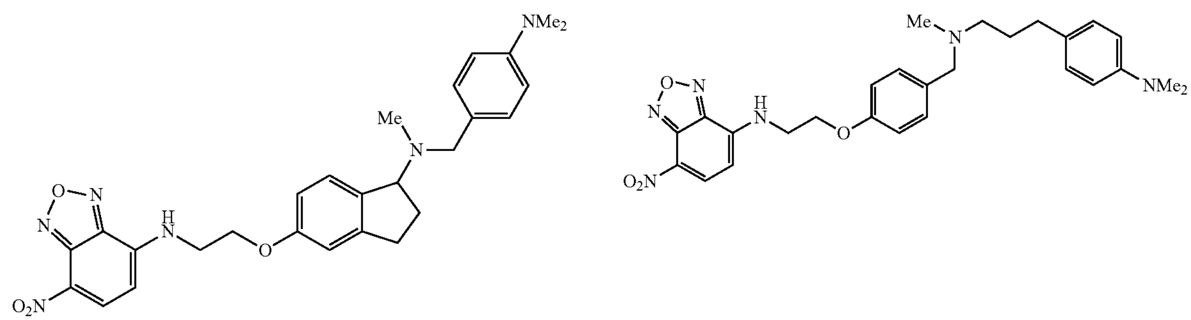
6
7
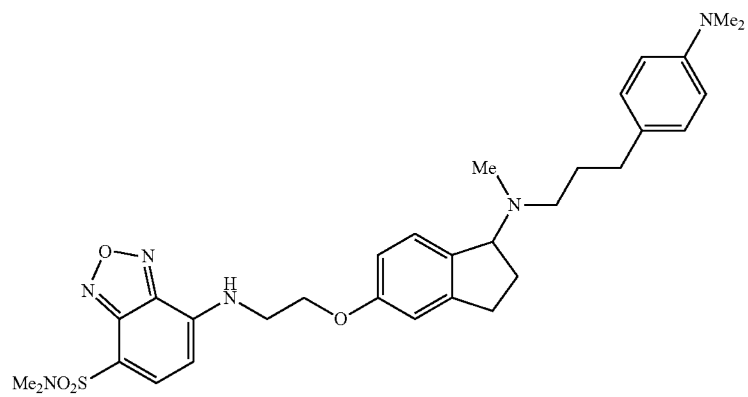
8
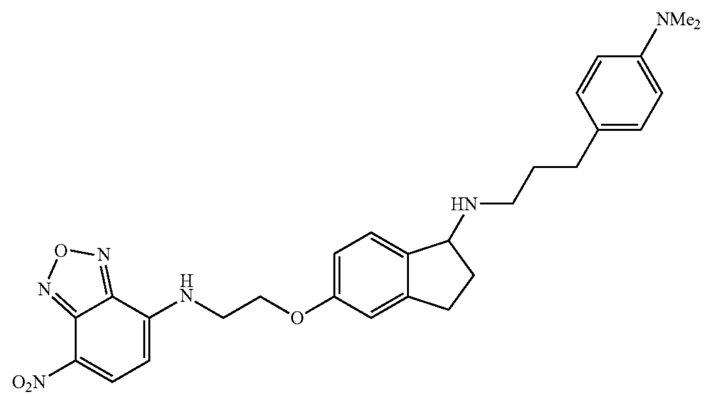

-continued

9

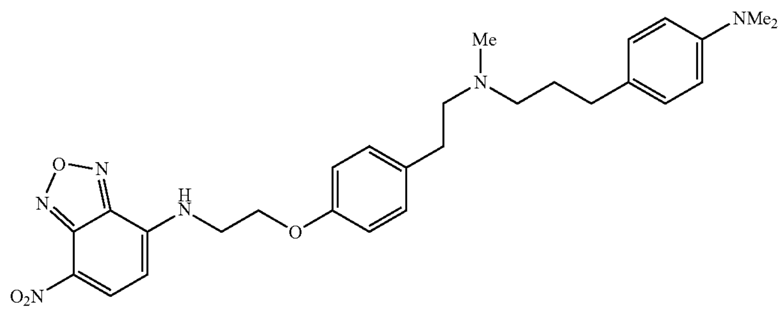

10

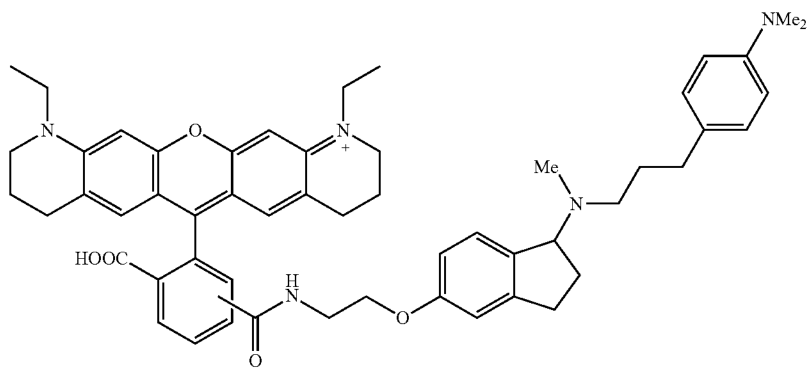

11

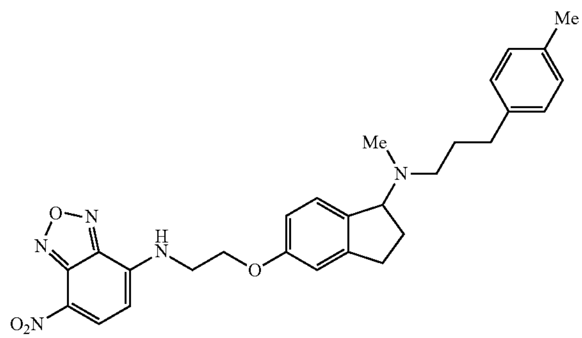

12

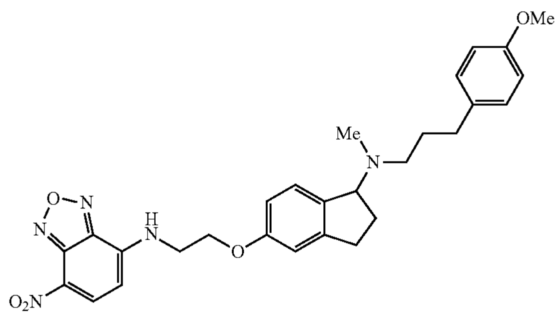

A compound expressed by Formula (1) conjugates with cellular vesicles derived from endosomes. Thus, the compound according to the embodiment can fluorescently stain endosomes or melanosomes in cells, exosomes released extracellularly, or the like. Further, when intracellular vesicles are stained, the compound according to the embodiment can specifically fluorescently stain intracellular vesicles in living cells. Moreover, the compound according to the embodiment conjugates with cellular vesicles to emit fluorescent, and the compound which is not in conjugation with cellular vesicles emits no fluorescence. Therefore, there is no need for operation of removing the compound which is not in conjugation with cellular vesicles, and thus sample loss can be suppressed.

Embodiment of Cellular Vesicle Staining Agent

The compound according to the embodiment described above can also be dissolved in a solvent and thus be used as a cellular vesicle staining agent. The solvent is not particularly limited as long as the solvent can dissolve the compound expressed by Formula (1) therein. The solvent may be, for example, acetone, DMSO, ethanol, an aqueous solution thereof, or the like.

The cellular vesicle staining agent according to the embodiment may optionally and additionally contain other fluorescence compounds that fluorescently stain elements different from cellular vesicles such as mitochondria, cell membranes, or the like, for example, other than the compound expressed by Formula (1). By using the compound expressed by Formula (1) and a fluorescent compound, it is possible to stain a plurality of elements at the same time. Further, with the interaction between the compound expressed by Formula (1) and the fluorescent compound, it is possible to sensitize the compound expressed by Formula (1) and improve specificity of the compound expressed by Formula (1) to cellular vesicles.

Embodiment of Method of Fluorescent Staining for Cellular Vesicles

A method of staining cellular vesicles according to the embodiment includes at least a staining step of staining cellular vesicles by using the compound expressed by Formula (1) or a cellular vesicle staining agent and a detection step of detecting the stained cellular vesicles in a sample and optionally and additionally includes an evaluation step of evaluating the sample after the detection step.

The staining step is to fluorescently stain cellular vesicles with the compound expressed by Formula (1). For example, when staining is performed on intracellular vesicles, the compound expressed by Formula (1) may be added to cells being cultured. Further, the cultured cells may be collected, and the compound expressed by Formula (1) may be added to the collected cells, which may be plated on a dish or the like. When staining is performed on extracellular vesicles such as exosomes, the compound expressed by Formula (1) may be added to a solution including extracellular vesicles.

In the staining step, for the amount of the compound expressed by Formula (1) to be added, the final concentration after the addition may be in a range of 0.01 μM to 10 μM, preferably in range of 0.1 μM to 1 μM.

The detecting step is to irradiate the sample with excitation light corresponding to a fluorescent group of the compound expressed by Formula (1) and detecting fluorescence emitted from the compound expressed by Formula (1) conjugated with cellular vesicles in the sample. For irradiation of excitation light, the same irradiation means as used in general fluorescence detection may be used, and a predetermined wavelength may be, for example, selected from a laser beam source of a fluorescence microscope as required. Detection of fluorescent may be performed from a lens barrel of the fluorescence microscope, and an image captured by a camera or the like installed in the fluorescence microscope may be displayed on display means such as a monitor. For some of the fluorescent groups of the compound expressed by Formula (1), even though fluorescence is unable to be sufficiently observed by visual observation through a lens barrel of the fluorescence microscope, the fluorescence may be observed through image capturing by a camera or the like. A filter that selectively passes light having a predetermined wavelength may be used as required.

Further, the method of fluorescent staining for cellular vesicles optionally and additionally includes an evaluating step of evaluating a sample. The evaluating step is to evaluate the sample by using cellular vesicles detected by the compound expressed by Formula (1). While what to evaluate depends on a sample, it is possible to evaluate cosmetics, pharmaceutical products, foods, or the like, for example. Moreover, it is possible to detect intracellular vesicles to evaluate the degree of cell differentiation or detect exosomes in body fluids to evaluate diseases or the like.

For example, when cosmetics or pharmaceutical products are evaluated, cellular vesicles are labeled with the compound expressed by Formula (1) in advance, and incorporation of the labeled cellular vesicles into the cells is detected and observed to evaluate the cosmetics or the pharmaceutical products in accordance with the presence of the cosmetics or the pharmaceutical products. For example, it is possible to evaluate pigmentation or skin diseases involved therewith based on incorporation of melanosomes, which are vesicles to store melanin, into keratinocytes. Further, it is possible to evaluate a food by measuring cellular vesicles included in the food. For example, it is possible to predict a food function from efficiency of miRNA incorporation into vesicles that affect intestinal functions.

Moreover, it is possible to evaluate the degree of cell differentiation by observing the distribution of cellular vesicles in cells. For example, melanocytes having a high melanosome content and melanocytes having a low melanosome content differ in their degree of differentiation. Thus, it is also possible to evaluate the degree of differentiation and the quality of cells by detecting melanosomes in melanocytes.

Further, exosomes reflect the features of the original cell from which the exosomes have been released. Further, cellular vesicles such as extracellularly released exosomes are included in biological tissues. Thus, exosomes in biological tissues can be used as a diagnostic marker of diseases or the like. It is therefore possible to collect biological tissues from a biological organism and measure cellular vesicles of the collected biological tissues by using the compound expressed by Formula (1) to evaluate diseases or the like. Therefore, the compound expressed by Formula (1) can also be applied to development of a clinical testing apparatus and a reagent and can also be used for a kit to measure cellular vesicles. Note that "biological tissue" in this specification includes a body fluid, a cell, and a tissue in a biological organism.

The compound, the cellular vesicle staining agent, and the method of fluorescent staining for cellular vesicles according to the embodiment achieve the following advantageous effects.

(1) The compound expressed by Formula (1) specifically conjugates with cellular vesicles. Further, the compound which is expressed by Formula (1) and does not conjugate with cellular vesicles emits no fluorescence. Therefore, since there is no need for operation of removing the unconjugated compound expressed by Formula (1) after specific fluorescent staining of cellular vesicles, sample loss can be suppressed.

(2) There is no need for operation of removing the unconjugated compound expressed by Formula (1), and cellular vesicles can be easily fluorescently stained by only adding the compound expressed by Formula (1).

(3) When containing a fluorescent compound other than the compound expressed by Formula (1), the cellular vesicle staining agent can stain a plurality of elements at the same time. Further, with the interaction between the compound expressed by Formula (1) and a fluorescent compound, it is possible to sensitize the compound expressed by Formula (1) and improve specificity of the compound expressed by Formula (1) to cellular vesicles.

(4) By detecting cellular vesicles by using the compound expressed by Formula (1), it is possible to evaluate cosmetics, pharmaceutical products, foods, degrees of differentiation of cells, disease, or the like.

Although embodiments disclosed in the present application will be specifically described with Examples presented below, these Examples are merely provided for describing the embodiment. These Examples are merely provided for illustration of the embodiment, which are intended neither to limit the scope of the invention disclosed in the present application nor to express limitation of the same.

EXAMPLE

Synthesis of Compound 1

Example 1

Compound 1 was synthesized according to the procedure described below.

[Formula 8]

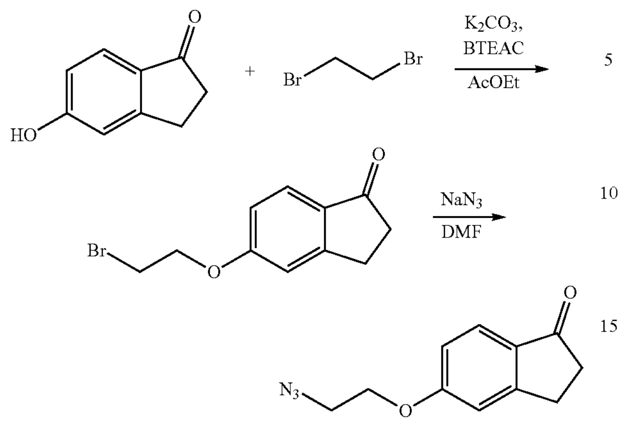

5-(2-bromoethoxy)-2,3-dihydro-1H-inden-1-one

After 5-hydroxy-1-indanone (745 mg, 5.03 mmol) was dissolved in ethyl acetate (15 mL), potassium carbonate (2.45 g, 17.7 mmol) suspended in ethyl acetate (15 mL), 1,2-dibromoethane (3.27 mL, 38.0 mmol), benzyltriethylammonium chloride (BTEAC) (121 mg, 531 μmol) were sequentially added, and the mixture was heated to reflux for 24 hours. The reaction liquid was allowed to be cooled to room temperature and then poured in ice water, extracted with ethyl acetate, washed with a saturated saline solution, and dried with anhydrous sodium sulfate. The residue obtained by concentrating the extracted liquid under reduced pressure was purified with column chromatography (silica gel, hexane/ethyl acetate=1/1), and a white solid of 5-(2-bromoethoxy)-2,3-dihydro-1H-inden-1-one (1.06 g, 4.16 mmol, 83%) was yielded.

$^1H$ NMR (400 MHz, $CDCl_3$) δ: 2.67 (m, 2H, $COCH_2$), 3.08 (br t, J=6 Hz, 2H, $ArCH_2$), 3.66 (t, J=6.4 Hz, 2H, $BrCH_2$), 4.35 (t, J=6.4 Hz, 2H, $OCH_2$), 6.89-6.93 (br m, 2H, ArH), 7.69 (d, J=9.2 Hz, 1H, ArH)

5-(2-azidoethoxy)-2,3-dihydro-1H-inden-1-one 5-(2-Bromoethoxy)-2,3-dihydro-1H-inden-1-one (410 mg, 1.61 mmol) was dissolved in N,N-dimethylformamide (5.0 mL), sodium azide (129 mg, 1.98 mmol) was added, and the mixture was heated to reflux for 35 minutes. The reaction liquid was allowed to be cooled to room temperature and then poured in water, extracted with diethyl ether, washed with a saturated saline solution, and dried with anhydrous sodium sulfate. The extracted liquid was concentrated under reduced pressure, and a red brown solid of 5-(2-azidoethoxy)-2,3-dihydro-1H-inden-1-one (346 mg, 1.59 mmol, 99%) was yielded.

$^1H$ NMR (400 MHz, $CDCl_3$) δ: 2.66-2.7 (m, 2H, $COCH_2$), 3.09 (br t, J=6 Hz, 26, $ArCH_2$), 3.63 (t, J=5 Hz, 2H, $N_3CH_2$), 4.21 (t, J=5 Hz, 2H, $OCH_2$), 6.90-6.94 (br m, 2H, ArH), 7.70 (d, J=9.2 Hz, 1H, ArH)

[Formula 9]

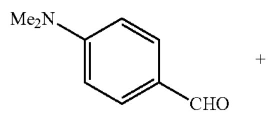

+

-continued

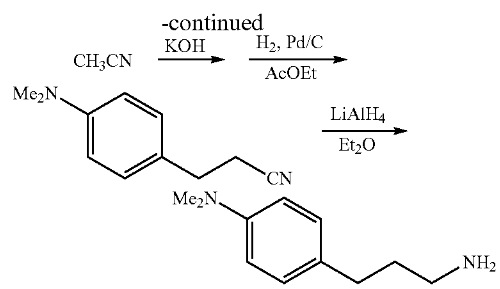

3-[4-(dimethylamino)phenyl]acrylonitrile

Potassium hydroxide (890 mg) was dissolved in acetonitrile (5.0 mL) under argon atmosphere, and the mixture was heated to reflux for 10 minutes. Subsequently, p-dimethylaminobenzaldehyde (2.03 g, 13.6 mmol) dissolved in acetonitrile (10.0 mL) was added, and the mixture was heated to reflux for 3 hours. The reaction liquid was allowed to be cooled to room temperature, water was then added, the mixture was concentrated under reduced pressure by a rotary evaporator. The residue was extracted with dichloromethane, washed with a saturated saline solution, and dried with anhydrous sodium sulfate. After the extracted liquid was concentrated under reduced pressure to the degree that the extracted liquid was not dried and hardened, ethyl acetate was added, the mixture was concentrated under reduced pressure twice in the same manner, and 3-[4-(dimethylamino)phenyl]acrylonitrile (2.40 g) was yielded. This compound was used in the next reaction without being purified.

3-[4-(dimethylamino)phenyl]propanenitrile

3-[4-(dimethylamino)phenyl]acrylonitrile (2.40 g) was dissolved in ethyl acetate (40.0 mL), and Pd/C (10%, 240 mg) was added to be reacted under hydrogen atmosphere at a balloon pressure at room temperature for 5 hours and 30 minutes. The reaction solution was filtered with celite, and the filtrate was concentrated under reduced pressure. The residue was purified with column chromatography (silica gel, hexane/ethyl acetate=3/1), and light yellow crystals of 3-[4-(dimethylamino)phenyl]propanenitrile (1.40 g, 8.03 mmol, two-step yield of 59%) was yielded.

$^1H$ NMR (400 MHz, $CDCl_3$) δ: 2.55 (t, J=7.4 Hz, 2H, $CH_2CN$), 2.86 (t, J=7.4 Hz, 2H, $ArCH_2$), 2.92 (s, 6H, $N(CH_3)_2$), 6.69 (d, J=8.7 Hz. 2H, ArH), 7.09 (d, J=8.7 Hz, 2H, ArH)

4-(3-aminopropyl)-N,N-dimethylaniline

3-[4-(dimethylamino)phenyl]propanenitrile (601 mg, 3.45 mmol) was dissolved in diethyl ether (3.5 mL) under argon atmosphere, and lithium aluminum hydride (391 mg, 10.3 mmol) was added under ice water bath to be reacted for 3 hours. Diethyl ether was added to the reacted mixture, and water (391 μL), 15% aqueous solution of sodium hydroxide (391 μL), and water (1.17 mL) were added in this order while being stirred. The reacted mixture was filtered with celite, the filtrate was then concentrated under reduced pressure, and yellow oily 4-(3-aminopropyl)-N,N-dimethylaniline (507 mg) was yielded.

[Formula 10]

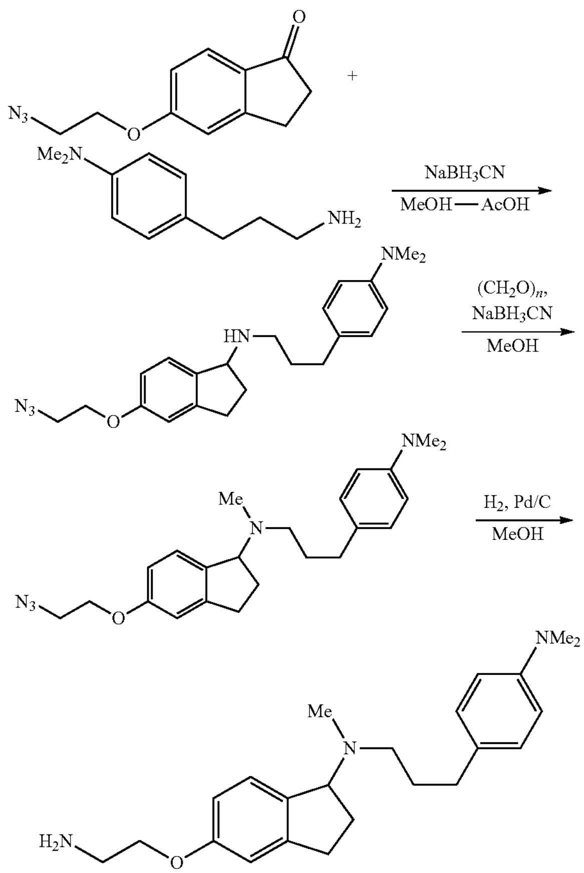

5-(2-azidoethoxy)-N-{3-[4-(dimethylamino)phenyl]propyl}-2,3-dihydro-1H-inden-1-amine 4-(3-aminopropyl)-N,N-dimethylaniline (67.6 mg, 379 μmol) was dissolved in methanol (600 μL), 5-(2-azidoethoxy)-2,3-dihydro-1H-inden-1-one (41.2 mg, 190 μmol), sodium cyanoborohydride (21.2 mg, 337 μmol), and acetic acid (30 μL) were added in this order, and the mixture was heated to reflux for 15 hours and 10 minutes. The reaction liquid was allowed to be cooled to room temperature, and 1 M hydrochloric acid was then added to quench excessive hydride. Subsequently, an aqueous solution of sodium hydroxide was added to the reaction liquid to make the mixture weakly basic, extraction was made with ethyl acetate, and the extract was dried with anhydrous sodium sulfate. The extracted liquid was concentrated under reduced pressure, the residue was purified with column chromatography (silica gel, acetone), and light yellow oily 5-(2-azidoethoxy)-N-{3-[4-(dimethylamino)phenyl]propyl}-2,3-dihydro-1H-inden-1-amine (36.3 mg, 95.6 μmol, 50%) was yielded.

$^1$H NMR (400 MHz, $CDCl_3$) δ: 1.75-1.86 (complex, 3H, $ArCH_2CH_2$), 2.35 (m, 1H, $ArCH_2CH_2$), 2.57 (dt, J=3.2 and 8.0 Hz, 2H, $ArCH_2$), 2.71 (t, J=7.1, 2H, $ArCH_2$), 2.7-2.8 (m, 1H), 2.90 (s, 6H, $N(CH_3)_2$), 2.90-2.99 (m, 1H), 3.56 (t, J=5 Hz, 2H, $N_3CH_2$), 4.12 (t, J=5 Hz, 2H, $OCH_2$), 4.15 (t, J=6.4 Hz, 1H, ArCHNH), 6.68 (d, J=8.4 Hz, 2H, ArH), 6.74 (d, J=8.2 Hz, 1H, ArH), 5.77 (s, 1H, ArH), 7.05 (d, J=8.4 Hz, 2H, ArH), 7.20 (d, J=8.2 Hz, 1H, ArH)

5-(2-azidoethoxy)-N-{3-[4-(dimethylamino)phenyl]propyl}-N-methyl-2,3-dihydro-1H-inden-1-amine 5-(2-azidoethoxy)-N-{3-[4-(dimethylamino)phenyl]propyl}-2,3-dihydro-1H-inden-1-amine (10.1 mg, 26.6 μmol) was dissolved in methanol (150 μL), and paraformaldehyde (4.9 mg) and sodium cyanoborohydride (19.6 mg, 312 μmol) were added in this order to be reacted at room temperature for 18 hours. Then, 1 M hydrochloric acid was added to the reaction liquid to quench excessive hydride. Subsequently, an aqueous solution of sodium hydroxide was added to the reaction liquid to make the mixture weakly basic, extraction was made with ethyl acetate, and the extract was dried with anhydrous sodium sulfate. The extracted liquid was concentrated under reduced pressure, the residue was purified with column chromatography (silica gel, acetone), and light yellow oily 5-(2-azidoethoxy)-N-{3-[4-(dimethylamino)phenyl]propyl}-N-methyl-2,3-dihydro-1H-inden-1-amine (5.4 mg, 14 μmol, 53%) was yielded.

$^1$H NMR (400 MHz, $CDCl_3$) δ: 1.72-1.84 (complex, 2H, $ArCH_2CH_2$), 1.98-2.05 (m, 2H, $ArCH_2CH_2$), 2.15 (s, 3H, $NCH_3$), 2.38-2.45 (m, 1H), 2.44-2.62 (complex, 2H), 2.7-2.8 (m, 1H), 2.89 (br, 8H), 3.57 (t, J=5.0 Hz, 2H, $N_3CH_2$), 4.13 (t, J=5.0 Hz, 2H, $OCH_2$), 4.35 (t, J=7.4 Hz, 1H, ArCHN), 6.68 (d, J=8.7 Hz, 2H, ArH), 6.75 (s, 1H, ArH), 6.75-6.78 (1H, ArH), 7.05 (d, J=8.7 Hz, 2H, ArH), 7.25-7.26 (1H, ArH)

5-(2-aminoethoxy)-N-{3-[4-(dimethylamino)phenyl]propyl}-N-methyl-2,3-dihydro-1H-inden-1-amine 5-(2-azidoethoxy)-N-{3-[4-(dimethylamino)phenyl]propyl}-N-methyl-2,3-dihydro-1H-inden-1-amine (22.4 mg, 57 μmol) was dissolved in methanol (500 μL), and Pd/C (10%, 4.2 mg) was added to be reacted under hydrogen atmosphere at a balloon pressure at room temperature for 6 hours and 20 minutes. The reacted mixture was filtered with celite, the filtrate was concentrated under reduced pressure, and yellow oily 5-(2-aminoethoxy)-N-{3-[4-(dimethylamino)phenyl]propyl}-N-methyl-2,3-dihydro-1H-inden-1-amine (17.2 mg) was yielded.

$^1$H NMR (400 MHz, $CDCl_3$) δ: 1.7-1.85 (complex, 2H, $ArCH_2CH_2$), 1.97-2.06 (m, 2H, $ArCH_2CH_2$), 2.16 (s, 3H, $NCH_3$), 2.37-2.62 (complex, 4H), 2.7-2.9 (complex, 2H), 2.89 (s, 6H), 3.06 (t, J=5.0 Hz, 2H, $H_2NCH_2$), 3.96 (t, J=5.0 Hz, 2H, $OCH_2$), 4.31-4.4 (br, 1H, ArCHN), 6.68 (d, J=8.7 Hz, 2H, ArH), 6.74 (s, 1H, ArH), 6.74-6.77 (1H, ArH), 7.05 (d, J=8.7 Hz, 2H, ArH), 7.25-7.26 (1H, ArH)

[Formula 11]

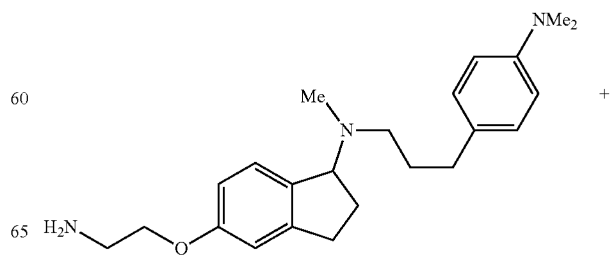

-continued

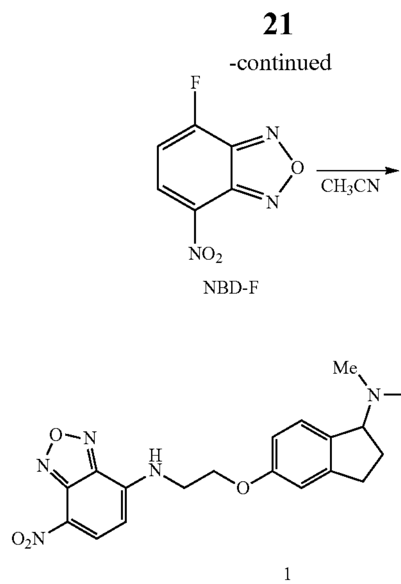

NBD-F

1

Compound 1

5-(2-aminoethoxy)-N-(3-(4-(dimethylamino)phenyl)propyl)-N-methyl-2,3-dihydro-1H-inden-1-amine (17.2 mg, 46.8 μmol) was dissolved in acetonitrile (500 μL), and subsequently, NBD-F (9.0 mg, 49 μmol) dissolved in acetonitrile (500 μL) was added to be reacted at room temperature for 5 hours and 30 minutes. The reaction solution was concentrated under reduced pressure, the residue was purified with silica gel column chromatography (silica gel, acetone), and red brown oily Compound 1 (19.7 mg, 37 μmol, 79%) was yielded.

$^1$H NMR (400 MHz, $CDCl_3$): δ: 1.72-1.83 (complex, 2H, $ArCH_2CH_2$), 1.98-2.07 (m, 2H, $ArCH_2CH_2$), 2.15 (s, 3H, $NCH_3$), 2.38-2.62 (complex, 3H, $NCH_2$ and $ArCH_2$), 2.71-2.94 (complex, 3H, $ArCH_2$), 2.89 (s, 6H, $N(CH_3)_2$), 3.86-3.92 (m, 2H, $HNCH_2$), 4.30 (t, J=5 Hz, 2H, $OCH_2$), 4.36 (t, J=6.7 Hz, 1H, ArCHN), 6.28 (d, J=8.5 Hz, 1H, ArH), 6.52 (br, 1H, ArH), 6.67 (d, J=8.5 Hz, 2H, ArH), 6.76 (s, 1H, ArH), 6.75-6.78 (1H, ArH), 7.05 (d, J=8.5 Hz, 2H, ArH), 8.51 (d, J=8.5 Hz, 1H, ArH)

Synthesis of Compound 2

Example 2

Compound 2 was synthesized according to the procedure described below.

[Formula 12]

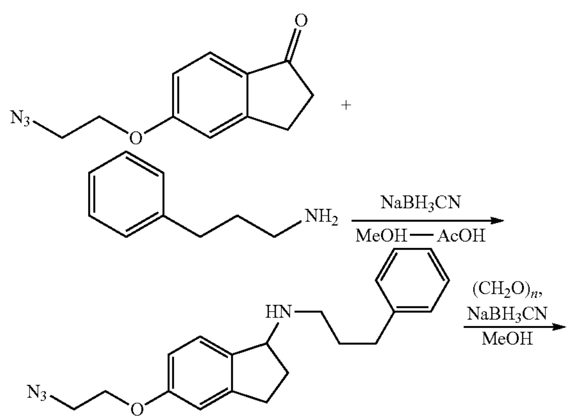

-continued

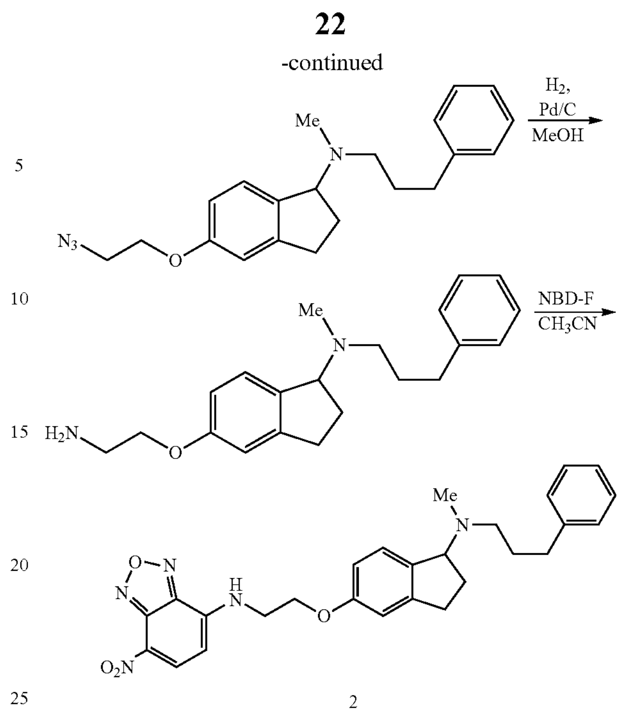

2

5-(2-azidoethoxy)-N-(3-phenylpropyl)-2,3-dihydro-1H-inden-1-amine

3-Phenylpropylamine (398 mg, 2.94 mmol) was dissolved in methanol (6.0 mL), 5-(2-azidoethoxy)-2,3-dihydro-1H-inden-1-one (320 mg, 1.47 mmol), sodium cyanoborohydride (111 mg, 1.77 mmol), and acetic acid (400 μL) were added in this order, and the mixture was heated to reflux for 18 hours. The reaction liquid was allowed to be cooled to room temperature, and 1 M hydrochloric acid was then added to quench excessive hydride. Subsequently, an aqueous solution of sodium hydroxide was added to the reaction liquid to make the mixture weakly basic, extraction was made with ethyl acetate, and the extract was dried with anhydrous sodium sulfate. The extracted liquid was concentrated under reduced pressure, the residue was purified with column chromatography (silica gel, acetone), and light yellow oily 5-(2-azidoethoxy)-N-(3-phenylpropyl)-2,3-dihydro-1H-inden-1-amine (141 mg, 419 μmol, 29%) was yielded. $^1$H NMR (400 MHz, $CDCl_3$) δ: 1.76-1.88 (complex, 3H, $ArCH_2CH_2$), 2.31-2.43 (m, 1H, $ArCH_2CH_2$), 2.6-2.8 (complex, 4H), 2.91-3.0 (complex, 2H), 3.56 (t, J=5 Hz, 2H, $N_3CH_2$), 4.12 (t, J=5 Hz, 2H, $OCH_2$), 4.15 (t, J=6 Hz, 1H, ArCHN), 6.74 (dd, J=8.2 and 2 Hz, 2H, ArH), 7.15-7.22 (complex, 4H, ArH), 7.26 (t, J=8.4 Hz, 2H, ArH)

5-(2-azidoethoxy)-N-methyl-N-(3-phenylpropyl)-2,3-dihydro-1H-inden-1-amine 5-(2-azidoethoxy)-N-(3-phenylpropyl)-2,3-dihydro-1H-inden-1-amine (79.0 mg, 235 μmol) was dissolved in methanol (1.0 mL), and paraformaldehyde (54.7 mg) and sodium cyanoborohydride (20.8 mg, 331 μmol) were added in this order to be reacted at room temperature for 18 hours. Then, 1 M hydrochloric acid was added to the reaction liquid to quench excessive hydride. Subsequently, an aqueous solution of sodium hydroxide was added to the reaction liquid to make the mixture weakly basic, extraction was made with ethyl acetate, and the extract was dried with anhydrous sodium sulfate. The extracted liquid was concentrated under reduced pressure, the residue was purified with column chromatography (silica gel, acetone), and light yellow oily 5-(2-azidoethoxy)-N-methyl-N-(3-phenylpropyl)-2,3-dihydro-1H-inden-1-amine (51 mg, 146 μmol, 62%) was yielded.

$^1H$ NMR (400 MHz, $CDCl_3$) δ: 1.76-1.86 (complex, 2H, $ArCH_2CH_2$), 1.98-2.05 (complex, 2H, $ArCH_2CH_2$), 2.16 (s, 3H, $NCH_3$), 2.35-2.48 (complex, 2H, $NCH_2$), 2.545-2.91 (complex, 4H, $ArCH_2$), 3.57 (t, J=5 Hz, 2H, $N_3CH_2$), 4.13 (t, J=5 Hz, 2H, $OCH_2$), 4.35 (t, J=7 Hz, 1H, ArCHN), 6.74-6.78 (br, 2H, ArH), 7.13-7.19 (complex, 3H, ArH), 7.21-7.28 (complex, 3H, ArH)

5-(2-aminoethoxy)-N-methyl-N-(3-phenylpropyl)-2,3-dihydro-1H-inden-1-amine 5-(2-azidoethoxy)-N-methyl-N-(3-phenylpropyl)-2,3-dihydro-1H-inden-1-amine (27.4 mg, 78 μmol) was dissolved in methanol (1.0 mL), Pd/C (10%, 2.8 mg) was added to be reacted under hydrogen atmosphere at a balloon pressure at room temperature for 7 hours and 30 minutes. The reacted mixture was filtered with celite, the filtrate was concentrated under reduced pressure, and yellow oily 5-(2-aminoethoxy)-N-methyl-N-(3-phenylpropyl)-2,3-dihydro-1H-inden-1-amine (25.3 mg) was yielded.

Compound 2

5-(2-aminoethoxy)-N-methyl-N-(3-phenylpropyl)-2,3-dihydro-1H-inden-1-amine (25.3 mg, 78 μmol) was dissolved in acetonitrile (500 μL), and subsequently, NBD-F (14.5 mg, 79 μmol) dissolved in acetonitrile (500 UL) was added to be reacted at room temperature for 15 hours. The reaction solution was concentrated under reduced pressure, the residue was purified with column chromatography (silica gel, acetone), and Compound 2 (24.3 mg, 50 μmol, 64%) was yielded.

$^1H$ NMR (400 MHz, $CDCl_3$) δ: 1.77-1.86 complex, 2H, $ArCH_2CH_2$), 1.98-2.07 (complex, 2H, $ArCH_2CH_2$), 2.16 (s, 3H, $NCH_3$), 2.43 (br t, J=7 Hz, 2H, $NCH_2$), 2.54-2.92 (complex, 4H, $ArCH_2$), 3.89 (br, 2H, $HNCH_2$), 4.30 (t, J=5 Hz, 2H, $OCH_2$), 4.36 (t, 1H, J=7 Hz, ArCHN), 6.28 (d, J=8.7 Hz, 1H, ArH), 6.75-6.78 (br, 2H, ArH), 7.13-7.18 (complex, 4H, ArH), 7.23-7.28 (complex, 1H, ArH), 8.51 (d, J=8.7 Hz, 1H, ArH)

Synthesis of Compound 3

Example 3

Compound 3 was synthesized according to the procedure described below.

[Formula 13]

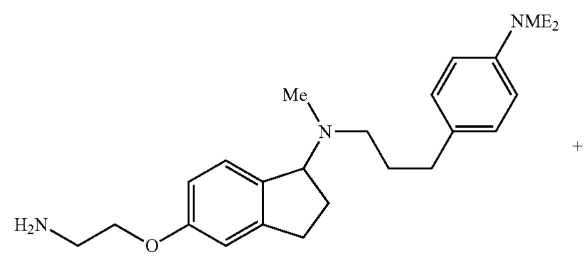

-continued

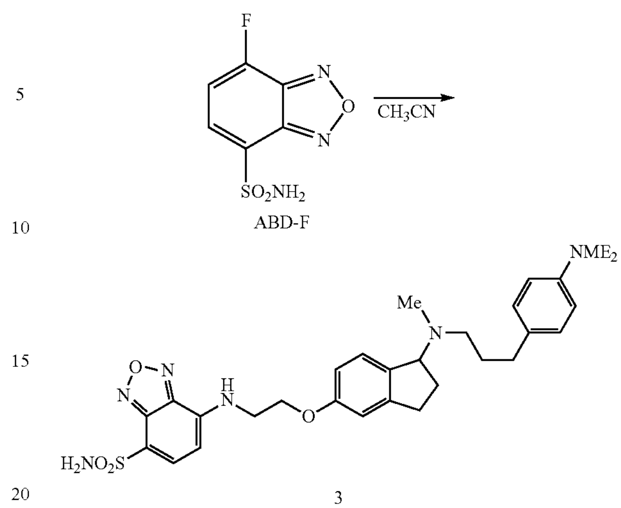

ABD-F

3

Compound 3

5-(2-aminoethoxy)-N-(3-(4-(dimethylamino)phenyl)propyl)-N-methyl-2,3-dihydro-1H-inden-1-amine (25.0 mg, 68 μmol) was dissolved in acetonitrile (500 μL), and subsequently, ABD-F (15.5 mg, 71 μmol) dissolved in acetonitrile (500 μL) was added to be reacted at room temperature for 4 hours and 10 minutes. The reaction solution was concentrated under reduced pressure, the residue was purified with column chromatography (silica gel, acetone), and red brown oily compound 3 (32.6 mg, 58 μmol, 85%) was yielded.

$^1H$ NMR (400 MHz, $CDCl_3$) δ: 1.75-1.84 (complex, 2H, $ArCH_2CH_2$), 2.0-2.08 (complex, 2H, $ArCH_2CH_2$), 2.16 (s, 3H, $NCH_3$), 2.41-2.6 (complex, 3H, $NCH_2$ and $ArCH_2$), 2.71-2.92 (complex, 3H, $ArCH_2$), 2.89 (s, 6H, $N(CH_3)_2$), 3.81 (t, J=5 Hz, 2H, $HNCH_2$), 4.27 (t, J=5 Hz, 2H, $OCH_2$), 4.34-4.41 (br, 1H, ArCHN), 6.01 (br t, J=8.2 Hz, 1H, ArH), 6.20 (d, J=8 Hz, 1H, ArH), 6.67 (d, J=8.7 Hz, 2H, ArH), 6.76 (s, 1H, ArH), 6.75-6.79 (1H, ArH), 7.04 (d, J=8.7 Hz, 2H, ArH), 7.95 (d, J=8 Hz, 1H, ArH)

Synthesis of Compound 4

Example 4

Compound 4 was synthesized according to the procedure described below.

[Formula 14]

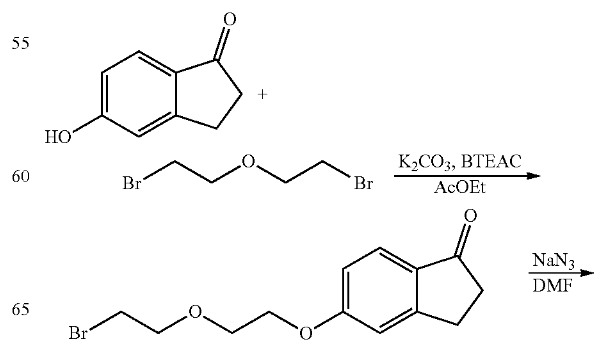

-continued

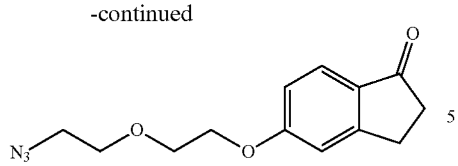

5-[2-(2-bromoethoxy) ethoxy]-2,3-dihydro-1H-inden-1-one

After 5-hydroxy-1-indanone (435 mg, 2.94 mmol) was dissolved in ethyl acetate (10 mL), potassium carbonate (1.47 g, 10.6 mmol) suspended in ethyl acetate (10 mL), bis(2-bromoethyl) ether (1.82 mL, 14.7 mmol), and benzyltriethylammonium chloride (76 mg, 334 μmol) were sequentially added, and the mixture was heated to reflux for 24 hours. The reaction liquid was allowed to be cooled to room temperature and then poured in ice water, extracted with ethyl acetate, washed with a saturated saline solution, and dried with anhydrous sodium sulfate. The residue obtained by concentrating the extracted liquid under reduced pressure was purified with column chromatography (silica gel, hexane/ethyl acetate 1/1), and a white solid of 5-[2-(2-bromoethoxy) ethoxy]-2,3-dihydro-1H-inden-1-one (654 mg, 2.19 mmol, 74%) was yielded.

$^1$H NMR (400 MHz, $CDCl_3$) δ: 2.66 (m, 2H, $COCH_2$), 3.07 (br t, J=6 Hz, 2H, $ArCH_2$), 3.49 (t, J=6.2 Hz, 2H, $BrCH_2$), 3.88 (t, J=6.4 Hz, 2H, $OCH_2$), 3.90 (t, J=5 Hz, 2H, $OCH_2$), 4.21 (t, J=5 Hz, 2H, $ArOCH_2$), 6.89-6.93 (br m, 2H, ArH), 7.68 (d, J=9.2 Hz, 1H, ArH)

5-[2-(2-azidoethoxy) ethoxy]-2,3-dihydro-1H-inden-1-one

5-[2-(2-bromoethoxy) ethoxy]-2,3-dihydro-1H-inden-1-one (403 mg, 1.35 mmol) was dissolved in N,N-dimethylformamide (5.0 mL), sodium azide (105 mg, 1.61 mmol) was added, and the mixture was heated to reflux for 1 hour and 30 minutes. The reaction liquid was allowed to be cooled to room temperature and then poured in water, extracted with diethyl ether, washed with a saturated saline solution, and dried with anhydrous sodium sulfate. The extracted liquid was concentrated under reduced pressure, and a red brown solid of 5-[2-(2-azidoethoxy) ethoxy]-2,3-dihydro-1H-inden-1-one (347 mg, 1.33 mmol, 99%) was yielded.

$^1$H NMR (400 MHz, $CDCl_3$) δ: 2.64-2.68 (m, 2H, $COCH_2$), 3.07 (br t, J=6 Hz, 2H, $ArCH_2$), 3.41 (t, J=5 Hz, 2H, $N_3CH_2$), 3.75 (t, J=5 Hz, 2H, $OCH_2$), 3.89 (t, J=4.6 Hz, 2H, $OCH_2$), 4.21 (t, J=4.6 Hz, 2H, $ArOCH_2$), 6.89-6.93 (br m, 2H, ArH), 7.67 (d, J=9.2 Hz, 1H, ArH)

[Formula 15]

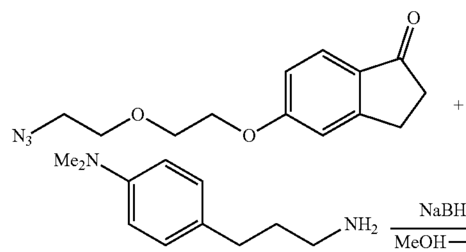

-continued

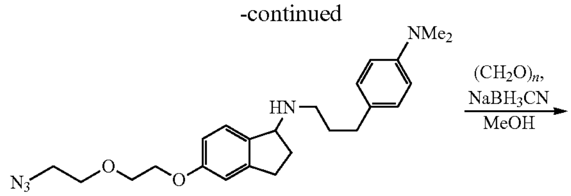

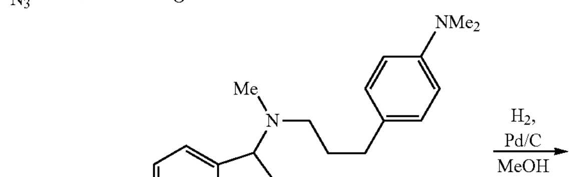

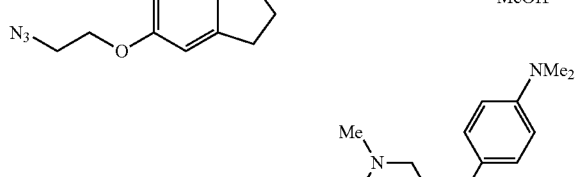

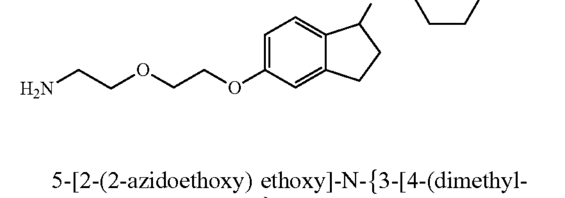

5-[2-(2-azidoethoxy) ethoxy]-N-{3-[4-(dimethylamino)phenyl]propyl}-2,3-dihydro-1H-inden-1-amine 4-(3-aminopropyl)-N,N-dimethylaniline (120 mg, 673 μmol) was dissolved in methanol (3.0 mL), 5-[2-(2-azidoethoxy) ethoxy]-2,3-dihydro-1H-inden-1-one (101 mg, 386 μmol), sodium cyanoborohydride (49.2 mg, 783 μmol), and acetic acid (100 μL) were added in this order, and the mixture was heated to reflux for 38 hours. The reaction liquid was allowed to be cooled to room temperature, and 1 M hydrochloric acid was then added to quench excessive hydride. Subsequently, an aqueous solution of sodium hydroxide was added to the reaction liquid to make the mixture weakly basic, extraction was made with ethyl acetate, and the extract was dried with anhydrous sodium sulfate. The extracted liquid was concentrated under reduced pressure, the residue was purified with column chromatography (silica gel, ethyl acetate), and light yellow oily 5-[2-(2-azidoethoxy) ethoxy]-N-{3-[4-(dimethylamino)phenyl]propyl}-2,3-dihydro-1H-inden-1-amine (105 mg, 248 μmol, 64%) was yielded.

$^1$H NMR (400 MHz, $CDCl_3$) δ: 1.75-1.85 (complex, 3H, $ArCH_2CH_2$), 2.31-2.4 (m, 1H, $ArCH_2CH_2$), 2.57 (dt, J=3 and 8 Hz, 2H, $ArCH_2$), 2.71 (t, J=7 Hz, 2H, $ArCH_2$), 2.7-2.8 (m, 1H), 2.90 (s, 6H, $N(CH_3)_2$), 2.89-3.0 (m, 1H), 3.40 (t, J=5 Hz, 2H, $N_3CH_2$), 3.74 (t, J=5 Hz, 2H, $OCH_2$), 3.84 (t, J=5 Hz, 2H, $OCH_2$), 4.12 (t, J=5 Hz, 2H, $OCH_2$), 4.09-4.18 (complex, 3H, $ArOCH_2$ and ArCHNH), 6.68 (d, J=8.7 Hz, 2H, ArH), 6.74 (dd, J=2 and 8.2 Hz, 1H, ArH), 6.77 (s, 1H, ArH), 7.05 (d, J=8.7 Hz, 2H, ArH), 7.18 (d, J=8.2 Hz, 1H, ArH)

5-[2-(2-azidoethoxy) ethoxy]-N-{3-[4-(dimethylamino)phenyl]propyl}-N-methyl-2,3-dihydro-1H-inden-1-amine 5-[2-(2-azidoethoxy) ethoxy]-N-{3-[4-(dimethylamino) phenyl]propyl}-2,3-dihydro-1H-inden-1-amine (13 mg, 31 μmol) was dissolved in methanol (300 UL), and paraformaldehyde (10.7 mg) and sodium cyanoborohydride (9.7 mg, 154 μmol) were added in this order to be reacted at room temperature for 17 hours. Then, 1 M hydrochloric acid was added to the reaction liquid to quench excessive hydride. Subsequently, an aqueous solution of sodium hydroxide was added to the reaction liquid to make the mixture weakly basic, extraction was made with ethyl acetate, and the extract was dried with anhydrous sodium sulfate. The extracted liquid was concentrated under reduced pressure, the residue was purified with column chromatography (silica gel, acetone), and light yellow oily 5-(2-(2-azidoethoxy)ethoxy)-N-(3-(4-(dimethylamino)phenyl)propyl)-N-methyl-2,3-dihydro-1H-inden-1-amine (9.8 mg, 22 μmol, 71%) was yielded.

$^1$H NMR (400 MHz, $CDCl_3$) δ: 1.7-1.82 (complex, 2H, $ArCH_2CH_2$), 1.96-2.05 (m, 2H, $ArCH_2CH_2$), 2.14 (s, 3H, $NCH_3$), 2.37-2.62 (complex, 4H), 2.7-2.8 (m, 1H), 2.89 (br, 8H), 3.4 (br, 2H, $N_3CH_2$), 3.74 (br, 2H, $OCH_2$), 3.85 (br, 2H, $OCH_2$), 4.12 (br, 2H, $ArOCH_2$), 4.34 (m, 1H, ArCHN), 6.67 (br, 2H, ArH), 6.75 (br, 2H, ArH), 6.75-6.78 (1H, ArH), 7.05 (br, 2H, ArH)

5-[2-(2-aminoethoxy)ethoxy]-N-{3-[4-(dimethylamino)phenyl]propyl}-N-methyl-2,3-dihydro-1H-inden-1-amine 5-[2-(2-azidoethoxy)ethoxy]-N-{3-[4-(dimethylamino)phenyl]propyl}-N-methyl-2,3-dihydro-1H-inden-1-amine (9.8 mg, 22 μmol) was dissolved in methanol (1 mL), and Pd/C (10%, 3.7 mg) was added to be reacted under hydrogen atmosphere at a balloon pressure at room temperature for 6 hours and 20 minutes. The reacted mixture was filtered with celite, the filtrate was concentrated under reduced pressure, and yellow oily 5-[2-(2-aminoethoxy)ethoxy]-N-{3-[4-(dimethylamino)phenyl]propyl}-N-methyl-2,3-dihydro-1H-inden-1-amine (8.8 mg) was yielded.

[Formula 16]

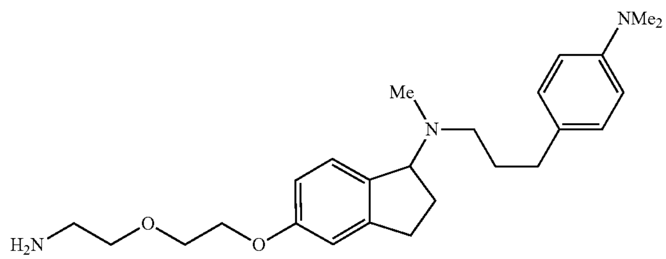

+

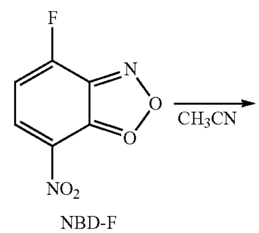

NBD-F

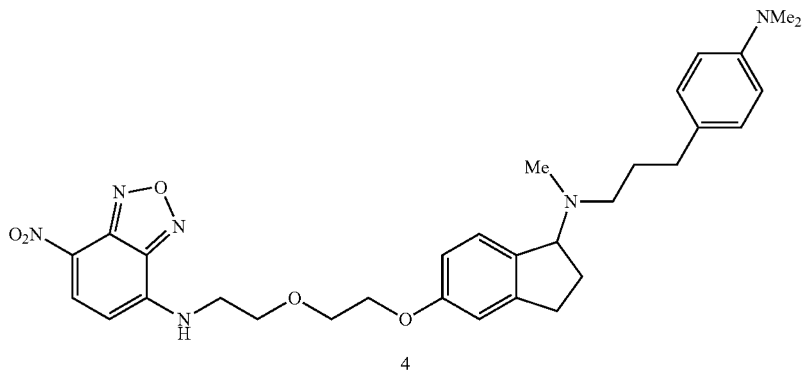

4

Compound 4

5-[2-(2-aminoethoxy) ethoxy]-N-{3-[4-(dimethylamino) phenyl]propyl}-N-methyl-2,3-dihydro-1H-inden-1-amine (8.8 mg, 21 μmol) was dissolved in acetonitrile (500 μL), and subsequently, NBD-F (4.2 mg, 23 μmol) dissolved in acetonitrile (500 μL) was added to be reacted at room solution was temperature for 15 hours. The reaction concentrated under reduced pressure, the residue was purified with silica gel column chromatography (silica gel, acetone), and red brown oily Compound 4 (4.3 mg, 7.5 μmol, 36%) was yielded.

$^1$H NMR (400 MHz, $CDCl_3$): δ: 1.74-1.85 (br, 2H, $ArCH_2CH_2$), 1.98-2.08 (m, 2H, $ArCH_2CH_2$), 2.16 (s, 3H, $NCH_3$), 2.41-2.6 (complex, 4H, $NCH_2$ and $ArCH_2$), 2.7-2.86 (complex, 2H, $ArCH_2$), 2.89 (s, 6H, $N(CH_3)_2$), 3.62-3.81 (m, 2H, $HNCH_2$), 3.88-3.95 (complex, 4H), 4.13 (t, J=5 Hz, 2H, $OCH_2$), 4.39 (br, 1H, ArCHN), 6.18 (d, J=8.5 Hz, 1H, ArH), 6.61 (br, 1H, ArH), 6.67 (d, J=8.4 Hz, 2H, ArH), 6.72 (s, 1H, ArH), 6.71-6.76 (1H, ArH), 7.04 (d, J=8.4 Hz, 2H, ArH), 8.44 (d, J=8.5 Hz, 1H, ArH)

Synthesis of Compound 5

Example 5

Compound 5 was synthesized according to the procedure described below.

[Formula 17]

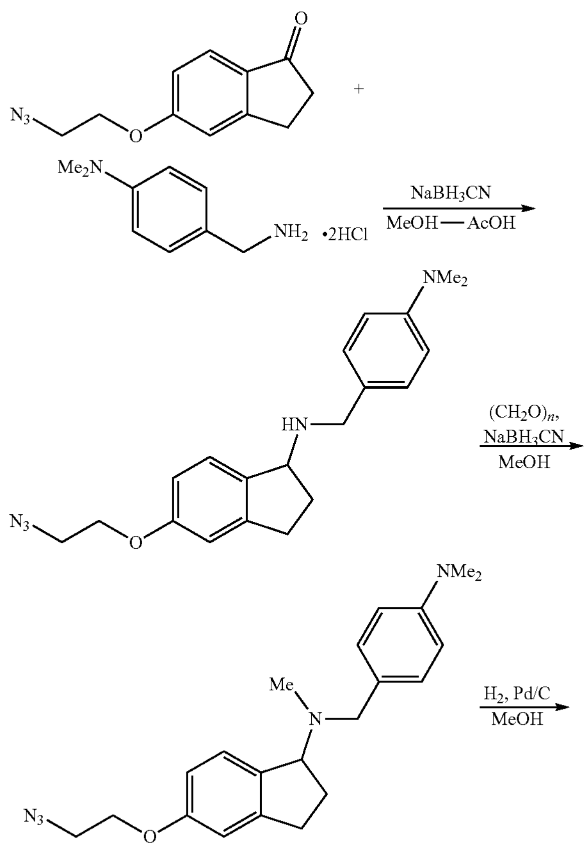

-continued

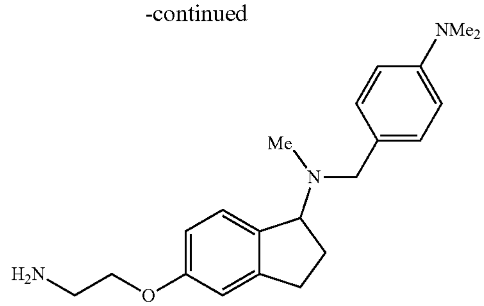

5-(2-azidoethoxy)-N-[4-(dimethylamino)benzyl]-2,3-dihydro-1H-inden-1-amine 4-(dimethylamino)benzylamine dihydrochloride (155 mg, 695 μmol) was dissolved in methanol (3.0 mL), triethylamine (216 μL), 5-(2-azidoethoxy)-2,3-dihydro-1H-inden-1-one (100 mg, 460 μmol), sodium cyanoborohydride (48.5 mg, 772 μmol), and acetic acid (100 μL) were added in this order, and the mixture was heated to reflux for 42 hours. The reaction liquid was allowed to be cooled to room temperature, and 1 M hydrochloric acid was then added to quench excessive hydride. Subsequently, an aqueous solution of sodium hydroxide was added to the reaction liquid to make the mixture weakly basic, extraction was made with ethyl acetate, and the extract was dried with anhydrous sodium sulfate. The extracted liquid was concentrated under reduced pressure, the residue was purified with column chromatography (silica gel, ethyl acetate), and light yellow oily 5-(2-azidoethoxy)-N-[4-(dimethylamino)benzyl]-2,3-dihydro-1H-inden-1-amine (130 mg, 370 μmol, 80%) was yielded.

$^1$H NMR (400 MHz, $CDCl_3$) δ: 1.88-2.0 and 2.35-2.45 (complex, each 1H, $ArCH_2CH_2$), 2.78 (dt, J=7.8 and 15.8 Hz, 1H, $ArCH_2$), 2.91 (s, 6H, $N(CH_3)_2$), 3.0 (ddd, J=5, 8.5, and 15.8 Hz, 1H, $ArCH_2$), 3.56 (t, J=5 Hz, 2H, $N_3CH_2$), 3.77 and 3.81 (d, J=12.8 Hz, 2H, $ArCH_2N$), 4.11 (t, J=5 Hz, 2H, $OCH_2$), 4.26 (t, J=6.4 Hz, 1H, ArCHN), 6.70 (d, J=8.7 Hz, 2H, ArH), 6.76 (d, J=8.3 Hz, 1H, ArH), 6.78 (br s, 1H, ArH), 7.22-7.25 (2H, ArH), 7.27 (d, J=8.3 Hz, 1H, ArH)

5-(2-azidoethoxy)-N-[4-(dimethylamino)benzyl]-N-methyl-2,3-dihydro-1H-inden-1-amine 5-(2-azidoethoxy)-N-[4-(dimethylamino)benzyl]-2,3-dihydro-1H-inden-1-amine (57.5 mg, 164 μmol) was dissolved in methanol (0.8 mL), paraformaldehyde (27.1 mg) and sodium cyanoborohydride (16.0 mg, 255 μmol) were added in this order to be reacted at room temperature for 7 hours. Then, 1 M hydrochloric acid was added to the reaction liquid to quench excessive hydride. Subsequently, an aqueous solution of sodium hydroxide was added to the reaction liquid to make the mixture weakly basic, extraction was made with ethyl acetate, and the extract was dried with anhydrous sodium sulfate. The extracted liquid was concentrated under reduced pressure, the residue was purified with column chromatography (silica gel, ethyl acetate), and light yellow oily 5-(2-azidoethoxy)-N-[4-(dimethylamino)benzyl]-N-methyl-2,3-dihydro-1H-inden-1-amine (58 mg, 159 μmol, 97%) was yielded.

$^1$H NMR (400 MHz, $CDCl_3$) δ: 1.6-1.8 and 2.0-2.11 (complex, each 1H, $ArCH_2CH_2$), 2.12 (s, 3H, $NCH_3$), 2.71-2.83 and 2.86-2.95 (complex, each 1H, $ArCH_2$), 2.91 (s, 6H, $N(CH_3)_2$), 3.32 (d, J=12.8 Hz, 1H, $ArCH_2$), 3.50 (d, J=12.8

Hz, 1H, $ArCH_2$), 3.57 (t, J=5 Hz, 2H, $N_3CH_2$), 4.13 (t, J=5 Hz, 2H, $OCH_2$), 4.40 (t, J=7.1 Hz, 1H, ArCHN), 6.70 (d, J=8.7 Hz, 2H, ArH), 6.76 (s, 1H, ArH), 6.78 (d, J=8.2 Hz, 1H, ArH), 7.21 (d, J=8.7 Hz, 2H, ArH), 7.33 (d, J=8.2 Hz, 1H, ArH)

5-(2-aminoethoxy)-N-[4-(dimethylamino)benzyl]-N-methyl-2,3-dihydro-1H-inden-1-amine 5-(2-azidoethoxy)-N-[4-(dimethylamino)benzyl]-N-methyl-2,3-dihydro-1H-inden-1-amine (28.7 mg, 79 μmol) was dissolved in methanol (1.5 mL), and Pd/C (10%, 6.5 mg) was added to be reacted under hydrogen atmosphere at a balloon pressure at room temperature for 6 hours and 50 minutes. The reacted mixture was filtered with celite, the filtrate was concentrated under reduced pressure, and yellow oily 5-(2-aminoethoxy)-N-[4-(dimethylamino)benzyl]-N-methyl-2,3-dihydro-1H-inden-1-amine (23.5 mg) was yielded. This compound was used in the next reaction without being purified.

[Formula 18]

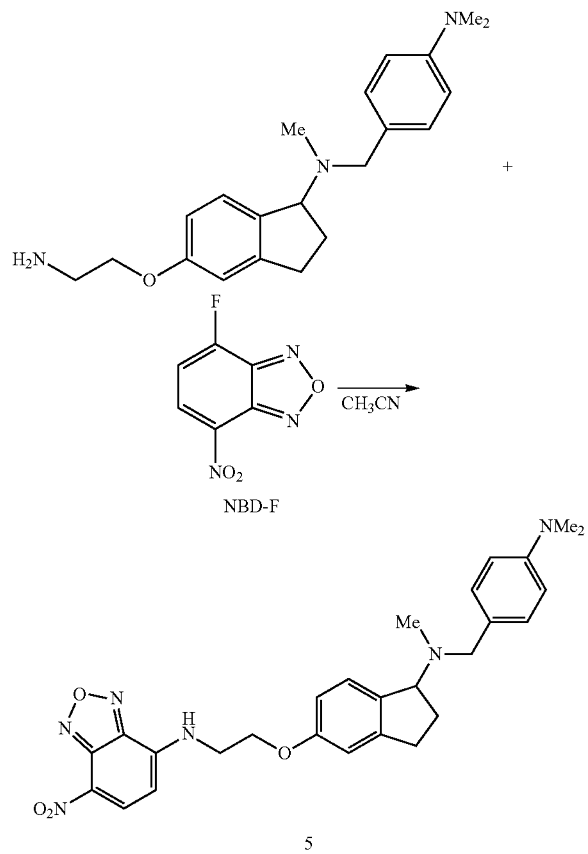

NBD-F

5

Compound 5

5-(2-aminoethoxy)-N-[4-(dimethylamino)benzyl]-N-methyl-2,3-dihydro-1H-inden-1-amine (23.0 mg, 68 μmol) was dissolved in acetonitrile (500 μL), and subsequently, NBD-F (14.4 mg, 79 μmol) dissolved in acetonitrile (500 μL) was added to be reacted at room temperature for 1 hour and 30 minutes. The reaction solution was concentrated under reduced pressure, the residue was purified with column chromatography (silica gel, ethyl acetate), and a red brown solid of Compound 5 (16.1 mg, 32 μmol, 47%) was yielded.

$^1H$ NMR (400 MHz, $CDCl_3$) δ: 2.0-2.2 (complex, 2H, $ArCH_2CH_2$), 2.12 (s, 3H, $NCH_3$), 2.71-2.93 (complex, 2H, $ArCH_2$), 2.91 (s, 6H, $N(CH_3)_2$), 3.31 (d, J=12.8 Hz, 1H, $ArCH_2N$), 3.49 (d, J=12.8 Hz, 1H, $ArCH_2N$), 3.89 (br, 2H, $HNCH_2$), 4.30 (t, J=5 Hz, 2H, $OCH_2$), 4.40 (br, 1H, ArCHN), 6.28 (d, J=7.8 Hz, 1H, ArH), 6.69 (d, J=7.8 Hz, 2H, ArH), 6.76 (s, 1H, ArH), 6.74-6.81 (1H, ArH), 7.20 (d, J=7.8 Hz, 2H, ArH), 7.35 (d, J=8.2 Hz, 1H), 8.51 (d, J=7.8 Hz, 1H)

Synthesis of Compound 6

Example 6

Compound 6 was synthesized according to the procedure described below.

[Formula 19]

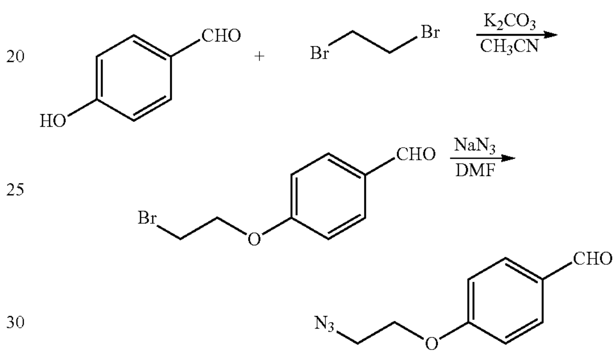

4-(2-bromoethoxy)benzaldehyde

After 4-hydroxybenzaldehyde (403 mg, 3.30 mmol) was dissolved in acetonitrile (25 mL), 1,2-dibromoethane (2.8 mL, 33.0 mmol) and potassium carbonate (825 mg, 5.97 mmol) were sequentially added, and the mixture was heated to reflux for 13 hours. The reaction liquid was allowed to be cooled to room temperature and then poured in ice water, extracted with diethyl ether, washed with a saturated saline solution, and dried with anhydrous sodium sulfate. The residue obtained by concentrating the extracted liquid under reduced pressure was purified with column chromatography (silica gel, hexane/ethyl acetate=3/1), and a light pink solid of 4-(2-bromoethoxy)benzaldehyde (559 mg, 2.44 mmol, 74%) was yielded.

$^1H$ NMR (400 MHz, $CDCl_3$) δ: 3.66 (t, J=6.2 Hz, 2H, $BrCH_2$), 4.37 (t, J=6.2 Hz, 2H, $OCH_2$), 7.01 (d, J=8.7 Hz, 2H, ArH), 7.84 (d, J=8.7 Hz, 2H, ArH), 9.89 (s, 1H, ArCHO)

4-(2-azidoethoxy)benzaldehyde 4-(2-bromoethoxy)benzaldehyde (402 mg, 1.75 mmol) was dissolved in N,N-dimethylformamide (5.0 mL), sodium azide (157 mg, 2.42 mmol) was added, and the mixture was heated to reflux for 20 minutes. The reaction liquid was allowed to be cooled to room temperature and then poured in water, extracted with diethyl ether, washed with a saturated saline solution, and dried with anhydrous sodium sulfate. The extracted liquid was concentrated under reduced pressure, and light yellow oily 4-(2-azidoethoxy)benzaldehyde (325 mg, 1.70 mmol, 97%) was yielded.

$^1H$ NMR (400 MHz, $CDCl_3$) δ: 3.64 (t, J=4.9 Hz, 2H, $N_3CH_2$), 4.22 (t, J=4.9 Hz, 2H, $OCH_2$), 7.02 (d, J=8.9 Hz, 2H, ArH), 7.85 (d, J=8.9 Hz, 1H, ArH), 9.89 (s, 1H, CHO)

[Formula 20]

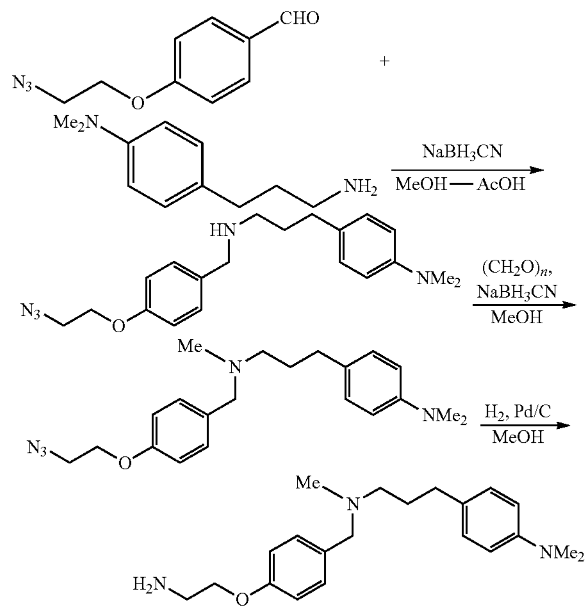

4-(3-{[4-(2-azidoethoxy)benzyl]amino}propyl)-N,N-dimethylaniline 4-(3-aminopropyl)-N,N-dimethylaniline (143 mg, 802 μmol) was dissolved in methanol (4 mL), 4-(2-azidoethoxy) benzaldehyde (100 mg, 523 μmol), sodium cyanoborohydride (63.3 mg, 1.01 mmol), and acetic acid (200 μL) were added in this order, and the mixture was heated to reflux for 375 hours. The reaction liquid was allowed to be cooled to room temperature, and 1 M hydrochloric acid was then added to quench excessive hydride. Subsequently, an aqueous solution of sodium hydroxide was added to the reaction liquid to make the mixture weakly basic, extraction was made with ethyl acetate, and the extract was dried with anhydrous sodium sulfate. The extracted liquid was concentrated under reduced pressure, the residue was purified with column chromatography (silica gel, ethyl acetate), and light yellow oily 4-(3-{[4-(2-azidoethoxy)benzyl]amino}propyl)-N,N-dimethylaniline (105 mg, 297 μmol, 57%) was yielded. This compound was used in the next reaction without being purified.

4-(3-{[4-(2-azidoethoxy)benzyl]methylamino}propyl)-N,N-dimethylaniline 4-(3-{[4-(2-azidoethoxy)benzyl] amino}propyl)-N,N-dimethylaniline (16.2 mg, 46 μmol) was dissolved in methanol (500 μL), paraformaldehyde (10 mg) and sodium cyanoborohydride (4.7 mg, 75 μmol) were added in this order to be reacted at room temperature for 16 hours. Then, 1 M hydrochloric acid was added to the reaction liquid to quench excessive hydride. Subsequently, an aqueous solution of sodium hydroxide was added to the reaction liquid to make the mixture weakly basic, extraction was made with ethyl acetate, and the extract was dried with anhydrous sodium sulfate. The extracted liquid was concentrated under reduced pressure, the residue was purified with column chromatography (silica gel, ethyl acetate), and light yellow oily 4-(3-{[4-(2-azidoethoxy)benzyl]methylamino}propyl)-N,N-dimethylaniline (7.8 mg, 21 μmol, 46%) was yielded.

$^1$H NMR (400 MHz, $CDCl_3$) δ: 1.79 (quin, J=7.5 Hz, 2H, $CH_2CH_2CH_2$), 2.16 (s, 3H, $NCH_3$), 2.39 (t, J=7.5 Hz, 2H, $NCH_2CH_2Ar$), 2.53 (t, J=7.5 Hz, 2H, $NCH_2CH_2Ar$), 2.90 (s, 6H, $N(CH_3)_2$), 3.42 (s, 2H, $ArCH_2N$), 3.58 (t, J=5.0 Hz, 2H, $N_3CH_2$), 4.14 (t, J=5 Hz, 2H, $ArOCH_2$), 6.68 (d, J=8.7 Hz, 2H, ArH), 6.86 (d, J=8.7 Hz, 2H, ArH), 7.05 (d, J=8.7 Hz, 2H, ArH), 7.22 (d, J=8.7 Hz, 2H, ArH)

4-(3-{[4-(2-aminoethoxy)benzyl]methylamino}propyl)-N,N-dimethylaniline 4-(3-{[4-(2-azidoethoxy)benzyl]methylamino}propyl)-N,N-dimethylaniline (7.2 mg, 20 μmol) was dissolved in methanol (1 mL), and Pd/C (10%, 4.7 mg) was added to be reacted under hydrogen atmosphere at a balloon pressure at room temperature for 3 hours and 40 minutes. The reacted mixture was filtered with celite, the filtrate was concentrated under reduced pressure, and yellow oily 4-(3-{[4-(2-aminoethoxy)benzyl]methylamino}propyl)-N,N-dimethylaniline (6.1 mg) was yielded. This compound was used in the next reaction without being purified.

$^1$H NMR (400 MHz, $CDCl_3$) δ: 1.78 (quin, J=7.7 Hz, 2H, $CH_2CH_2CH_2$), 2.15 (s, 3H, $NCH_3$), 2.38 (t, J=7.7 Hz, 2H, $NCH_2CH_2CH_2$), 2.53 (t, J=7.7 Hz, 2H, $CH_2CH_2CH_2Ar$), 2.90 (s, 6H, $N(CH_3)_2$), 3.07 (t, J=5 Hz, 2H, $H_2NCH_2$), 3.40 (s, 2H, $ArCH_2N$), 3.97 (t, J=5 Hz, 2H, $ArOCH_2$), 6.68 (d, J=8.7 Hz, 2H, ArH), 6.85 (d, J=8.7 Hz, 2H, ArH), 7.05 (d, J=8.7 Hz, 2H, ArH), 7.20 (d, J=8.7 Hz, 2H, ArH)

[Formula 21]

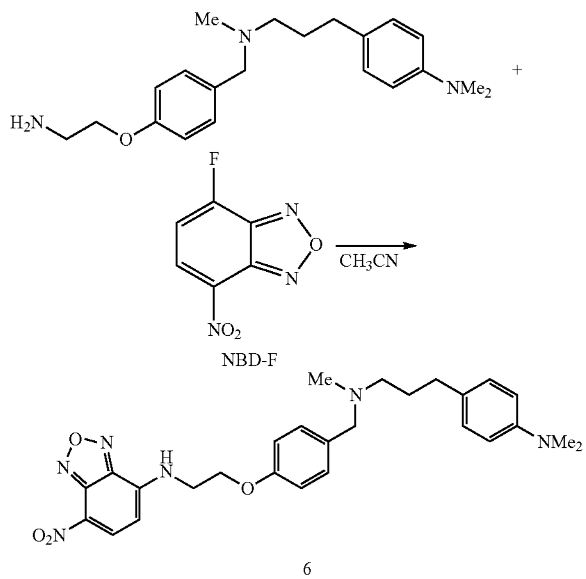

NBD-F

6

Compound 6

4-(3-{[4-(2-aminoethoxy)benzyl]methylamino}propyl)-N,N-dimethylaniline (5.9 mg, 17 μmol) was dissolved in acetonitrile (300 μL), and subsequently, NBD-F (3.5 mg, 19 μmol) dissolved in acetonitrile (300 μL) was added to be reacted at room temperature for 13 hours. An aqueous solution of saturated sodium bicarbonate was added to the reaction solution, extraction was made with ethyl acetate, and the extract was dried with anhydrous sodium sulfate. The extracted liquid was concentrated under reduced pressure, the residue was purified with column chromatography (silica gel, acetone), and a red brown solid of Compound 6 (6.6 mg, 13 μmol, 76%) was yielded.

$^1H$ NMR (400 MHz, $CDCl_3$) δ: 1.78 (quin, J=7.6 Hz, 2H, $CH_2CH_2CH_2$), 2.15 (s, 3H, $NCH_3$), 2.39 (t, J=7.6 Hz, 2H, $NCH_2CH_2CH_2$), 2.53 (t, J=7.6 Hz, 2H, $CH_2CH_2CH_2Ar$), 2.89 (s, 6H, $N(CH_3)_2$), 3.41 (s, 2H, $ArCH_2N$), 3.86-3.92 (m, 2H, $HNCH_2CH_2O$), 4.31 (t, J=5 Hz, 2H, $ArOCH_2$), 6.28 (d, J=8.7 Hz, 1H, ArH), 6.68 (d, J=8.7 Hz, 2H, ArH), 6.87 (d, J=8.7 Hz, 2H, ArH), 7.04 (d, J=8.7 Hz, 2H, ArH), 8.51 (d, J=8.7 Hz, 2H, ArH)

Synthesis of Compound 7

Example 7

Compound 7 was synthesized according to the procedure described below.

[Formula 22]

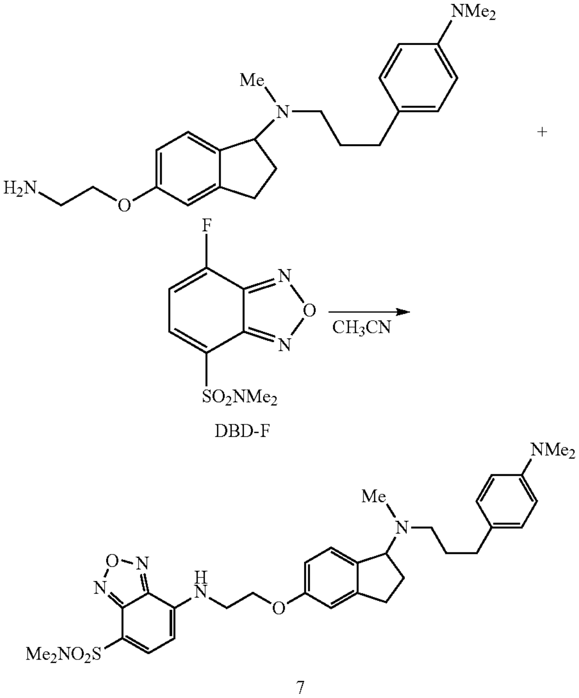

Compound 7

5-(2-aminoethoxy)-N-(3-(4-(dimethylamino)phenyl)propyl)-N-methyl-2,3-dihydro-1H-inden-1-amine (16.2 mg, 44 μmol) was dissolved in acetonitrile (500 μL), and subsequently, DBD-F (11.7 mg, 48 μmol) dissolved in acetonitrile (500 μL) was added to be reacted at room temperature for 15 hours and 20 minutes. The reaction solution was concentrated under reduced pressure, the residue was purified with column chromatography (silica gel, ethyl acetate), and red brown oily Compound 7 (20.7 mg, 35 μmol, 80%) was yielded.

$^1H$ NMR (400 MHz, $CDCl_3$) δ: 1.72-1.84 (br m, 2H, $ArCH_2CH_2$), 1.98-2.07 (complex, 2H, $ArCH_2CH_2$), 2.16 (s, 3H, $NCH_3$), 2.36-2.93 (complex, 6H, $NCH_2$ and $ArCH_2$), 2.86 (s, 6H, $N(CH_3)_2$), 2.89 (s, 6H, $N(CH_3)_2$), 3.80 (m, 2H, $HNCH_2$), 4.27 (t, J=5 Hz, 2H, $OCH_2$), 4.3-4.4 (br, 1H, ArCHN), 5.99 (br, 1H, ArH), 6.23 (d, J=7.8 Hz, 1H, ArH), 6.68 (d, J=8.3 Hz, 2H, ArH), 6.73-6.8 (complex, 2H, ArH), 7.05 (d, J=8.7 Hz, 2H, ArH), 7.91 (d, J=7.8 Hz, 1H, ArH)

Synthesis of Compound 8

Example 8

Compound 8 was synthesized according to the procedure described below.

[Formula 23]

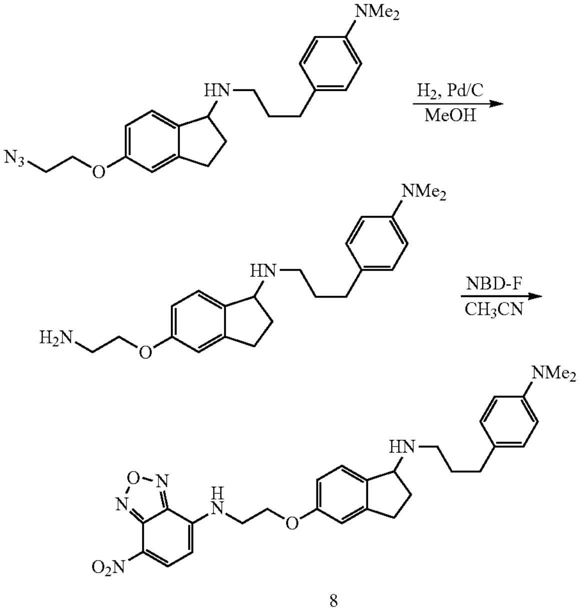

5-(2-aminoethoxy)-N-{3-[4-(dimethylamino)phenyl]propyl}-2,3-dihydro-1H-inden-1-amine 5-(2-azidoethoxy)-N-{3-[4-(dimethylamino)phenyl]propyl}-2,3-dihydro-1H-inden-1-amine (33.4 mg, 88 μmol) was dissolved in methanol (1.5 mL), and Pd/C (10%, 13.4 mg) was added to be reacted under hydrogen atmosphere at a balloon pressure at room temperature for 6 hours and 20 minutes. The reacted mixture was filtered with celite, the filtrate was concentrated under reduced pressure, and yellow oily 5-(2-aminoethoxy)-N-{3-[4-(dimethylamino)phenyl]propyl}-2,3-dihydro-1H-inden-1-amine (30.3 mg) was yielded. This compound was used in the next reaction without being purified.

$^1H$ NMR (400 MHz, $CDCl_3$) δ: 1.76-1.88 (1H, $ArCH_2CH_2$), 1.80 (quin, J=7.3 Hz, 2H, $ArCH_2CH_2$), 2.31-2.41 (complex, 1H, $ArCH_2CH_2$), 2.51-2.62 (m, 2H), 2.72 (t, J=7.1 Hz, 2H), 2.72-2.81 (m, 1H), 2.90 (s, 6H, $N(CH_3)_2$), 2.9-2.99 (br m, 1H), 3.05 (t, J=5.0 Hz, 2H, $H_2NCH_2$), 3.96 (t, J=5.0 Hz, 2H, $OCH_2$), 4.12-4.17 (m, 1H, ArCHN), 6.68 (d, J=8.2 Hz, 2H, ArH), 6.73 (d, J=8 Hz, 1H, ArH), 6.77 (s, 1H, ArH), 7.06 (d, J=8.2 Hz, 2H, ArH), 7.19 (d, J=8 Hz, 1H, ArH)

Compound 8

5-(2-aminoethoxy)-N-(3-(4-(dimethylamino)phenyl)propyl)-2,3-dihydro-1H-inden-1-amine (28.2 mg, 80 μmol) was dissolved in acetonitrile (500 μL), and subsequently, NBD-F (14.6 mg, 80 μmol) dissolved in acetonitrile (500 μL) was added to be reacted at room temperature for 30 minutes. An aqueous solution of saturated sodium bicarbonate was added to the reaction solution, extraction was made with ethyl acetate, and the extract was dried with anhydrous sodium sulfate. The extracted liquid was concentrated under reduced pressure, the residue was purified with thin-layer chromatography (silica gel, acetone), and red brown oily Compound 8 (24.3 mg, 47 μmol, 59%) was yielded.

$^1H$ NMR (400 MHz, $CDCl_3$): δ: 1.7-1.91 (br, 1H, $ArCH_2CH_2$), 1.82 (quin, J=7.4 Hz, 2H, $ArCH_2CH_2$), 2.32-2.41 (m, 1H, $ArCH_2CH_2$), 2.52-2.6 (complex, 2H, $NCH_2$ and $ArCH_2$), 2.72 (t, J=7.4 Hz, 2H, $ArCH_2$), 2.74-2.81 (complex, 1H, $ArCH_2CH_2$), 2.88-3.0 (1H), 2.89 (s, 6H, $N(CH_3)_2$), 3.86-3.92 (t, J=5 Hz, 2H, $HNCH_2CH_2O$), 4.19 (t, J=6.4 Hz, 1H, ArCHN), 4.28 (t, J=5 Hz, 2H, $OCH_2$), 6.28 (d, J=8.7 Hz, 1H, ArH), 6.67 (d, J=8.7 Hz, 2H, ArH), 6.74 (d, J=8.7 Hz, 2H, ArH), 6.77 (s, 1H, ArH), 7.04 (d, J=8.7 Hz, 2H, ArH), 8.50 (d, J=8.7 Hz, 1H, ArH)

Synthesis of Compound 9

Example 9

Compound 9 was synthesized according to the procedure described below.

[Formula 24]

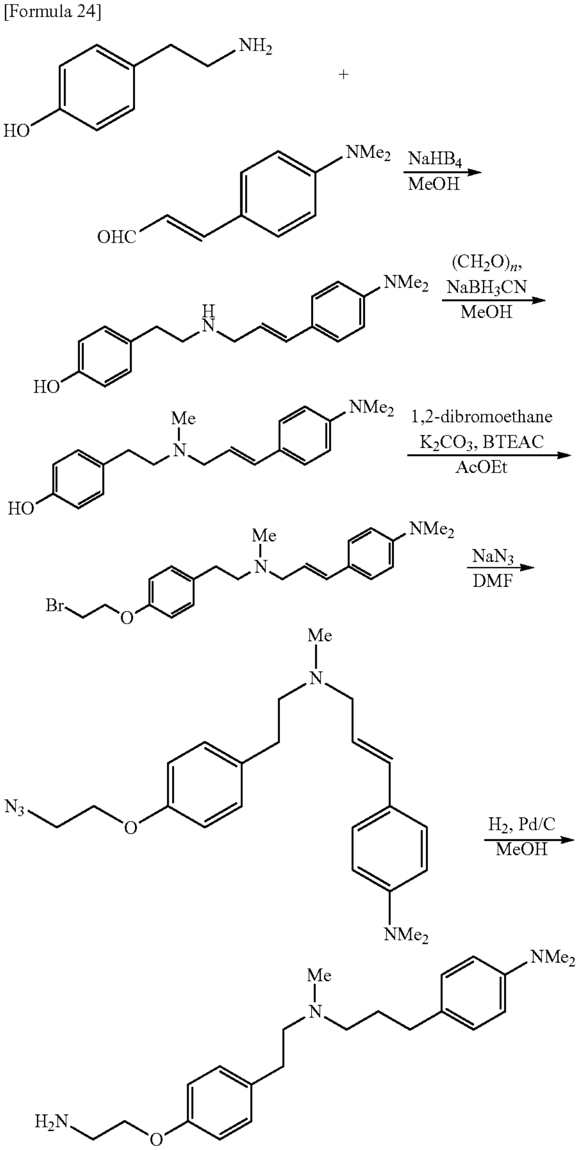

(E)-4-[2-({3-[4-(dimethylamino)phenyl]allyl}amino)ethyl]phenol

Tyramine (698 mg, 5.09 mmol) and 4-(dimethylamino) cinnamaldehyde (910 mg, 5.19 mmol) were dissolved in methanol (20 mL), 3 Å molecular sieve (969 mg) was added, and the mixture was stirred at room temperature for 22 hours. Subsequently, the reaction container was cooled to 0° C., and sodium borohydride (392 mg, 10.4 mmol) was added. Furthermore, methanol (26 mL) was added to the reaction solution, and the mixture was stirred at room temperature for 42 hours. The reacted mixture was filtered with celite, the filtrate was then concentrated under reduced pressure, and a yellow solid of (E)-4-[2-({3-[4-(dimethylamino)phenyl]allyl}amino)ethyl]phenol (1.44 g) was yielded. This compound was used in the next reaction without being purified.

(E)-4-[2-({3-[4-(dimethylamino)phenyl]allyl}(methyl)amino)ethyl]phenol (E)-4-[2-({3-[4-(dimethylamino)phenyl]allyl}amino)ethyl]phenol (1.43 g) was dissolved in methanol (35 mL), paraformaldehyde (930 mg) and sodium cyanoborohydride (389 mg, 6.19 mmol) were added in this order to be reacted at room temperature for 17 hours. Then, 1 M hydrochloric acid was added to the reaction liquid to quench excessive hydride. Subsequently, an aqueous solution of sodium hydroxide was added to the reaction liquid to make the mixture weakly basic, the reaction solution was concentrated under reduced pressure, extraction was then made with ethyl acetate, and the extract was dried with anhydrous sodium sulfate. The extracted liquid was concentrated under reduced pressure, the residue was purified with column chromatography (silica gel, acetone), and light yellow oily (E)-4-[2-({3-[4-(dimethylamino)phenyl]allyl}(methyl)amino)ethyl]phenol (796 mg, 2.56 mmol, two-step yield of 50%) was yielded.

$^1H$ NMR (400 MHz, $CDCl_3$) δ: 2.33 (s, 3H, $NCH_3$), 2.62 (dd, J=6.2 and 9.6 Hz, 2H, $NCH_2CH_2Ar$), 2.74 (dd, J=6.2 and 9.6 Hz, 2H, $NCH_2CH_2Ar$), 2.94 (s, 6H, $N(CH_3)_2$), 3.19 (d, J=6.9 Hz, 2H, $NCH_2CH{=}CH$), 6.05 (dt, J=6.9 and 16 Hz, 1H, $ArCH{=}CHCH_2$), 6.41 (d, J=16 Hz, 1H, $ArCH{=}CH$), 6.67 (d, J=8.7 Hz, 2H, ArH), 6.71 (d, J=8.3 Hz, 2H, ArH), 7.04 (d, J=8.3 Hz, 2H, ArH), 7.26 (2H, ArH).

(E)-4-(3-{[4-(2-bromoethoxy)phenethyl](methyl)amino}prop-1-en-1-yl)-N,N-dimethylaniline After (E)-4-[2-({3-[4-(dimethylamino)phenyl]allyl}(methyl)amino)ethyl]phenol (390 mg, 1.26 mmol) was dissolved in ethyl acetate (5.0 mL), potassium carbonate (653 mg, 4.73 mmol) suspended in ethyl acetate (12 mL), 1,2-dibromoethane (698 μL, 8.10 mmol), and benzyltriethylammonium chloride (BTEAC) (33.1 mg, 145 μmol) were sequentially added, and the mixture was heated to reflux for 17 hours. The reaction liquid was allowed to be cooled to room temperature and then poured in ice water, extracted with ethyl acetate, washed with a saturated saline solution, and dried with anhydrous sodium sulfate. The residue obtained by concentrating the extracted liquid under reduced pressure was purified with column chromatography (silica gel, acetone/ethyl acetate/triethylamine=100/100/3), and a yellow solid of (E)-4-(3-{[4-(2-bromoethoxy)phenethyl](methyl)amino}prop-1-en-1-yl)-N,N-dimethylaniline (361 mg, 865 μmol, 69%) was yielded.

$^1H$ NMR (400 MHz, $CDCl_3$) δ: 2.33 (s, 3H, $NCH_3$), 2.58-2.64 (m, 2H, $NCH_2CH_2Ar$), 2.71-2.78 (m, 2H, $NCH_2CH_2Ar$), 2.94 (s, 6H, $(CH_3)_2$), 3.19 (d, J=6.9 Hz, 2H, $NCH_2CH{=}CH$), 3.61 (t, J=6.2 Hz, 2H, $BrCH_2$), 4.25 (t, J=6.2 Hz, 2H, $ArOCH_2$), 6.05 (dt, J=6.9 and 16 Hz, 1H, $ArCH{=}CHCH_2$), 6.41 (d, J=16 Hz, 1H, $ArCH{=}CH$), 6.67 (d, J=8.7 Hz, 2H, ArH), 6.73 (d, J=8.2 Hz, 2H, ArH), 7.05 (d, J=8.2 Hz, 2H, ArH), 7.25 (2H, ArH).

(E)-4-(3-{[4-(2-azidoethoxy)phenethyl](methyl)amino}prop-1-en-1-yl)-N,N-dimethylaniline (E)-4-(3-{[4-(2-bromoethoxy)phenethyl](methyl)amino}prop-1-en-1-yl)-N,N-dimethylaniline (290 mg, 695 μmol) was dissolved in N,N-dimethylformamide (3.0 mL), and sodium azide (71.7 mg, 1.10 mmol) was added to be reacted at 90° C. for 1 hour. The reaction liquid was allowed to be cooled to room temperature and then poured in water, extracted with diethyl ether, washed with a saturated saline solution, and dried with anhydrous sodium sulfate. The residue obtained by concentrating the extracted liquid under reduced pressure was purified with column chromatography (silica gel, hexane/ethyl acetate=1/1), and a yellow solid of (E)-4-(3-{[4-(2-azidoethoxy)phenethyl](methyl)amino}prop-1-en-1-yl)-N,N-dimethylaniline (206 mg, 543 μmol, 78%) was yielded.

$^1H$ NMR (400 MHz, $CDCl_3$) δ: 2.33 (s, 3H, $NCH_3$), 2.56-2.66 (br, 2H, $NCH_2CH_2Ar$), 2.7-2.8 (br, 2H, $NCH_2CH_2Ar$), 2.94 (s, 6H, $N(CH_3)_2$), 3.19 (d, J=6.9 Hz, 2H, $NCH_2CH{=}CH$), 3.57 (t, J=4.8 Hz, 2H, $N_3CH_2$), 4.11 (t, J=4.8 Hz, 2H, $ArOCH_2$), 6.05 (dt, J=6.9 and 15.6 Hz, 1H, $ArCH{=}CHCH_2$), 6.41 (d, J=15.6 Hz, 1H, $ArCH{=}CH$), 6.67 (d, J=8.5 Hz, 2H, ArH), 6.83 (d, J=8.7 Hz, 2H, ArH), 7.11 (d, J=8.5 Hz, 2H, ArH), 7.25 (2H, ArH).

4-(3-{[4-(2-aminoethoxy)phenethyl](methyl)amino}propyl)-N,N-dimethylaniline (E)-4-(3-{[4-(2-azidoethoxy)phenethyl](methyl)amino}prop-1-en-1-yl)-N,N-dimethylaniline (20.5 mg, 54 μmol) was dissolved in methanol (1.0 mL), and Pd/C (10%, 5.8 mg) was added to be reacted under hydrogen atmosphere at a balloon pressure at room temperature for 15 hours and 50 minutes. The reacted mixture was filtered with celite, the filtrate was concentrated under reduced pressure, and yellow oily 4-(3-{[4-(2-aminoethoxy)phenethyl](methyl)amino}propyl)-N,N-dimethylaniline (17.8 mg, 93%) was yielded. This compound was used in the next reaction without being purified.

[Formula 25]

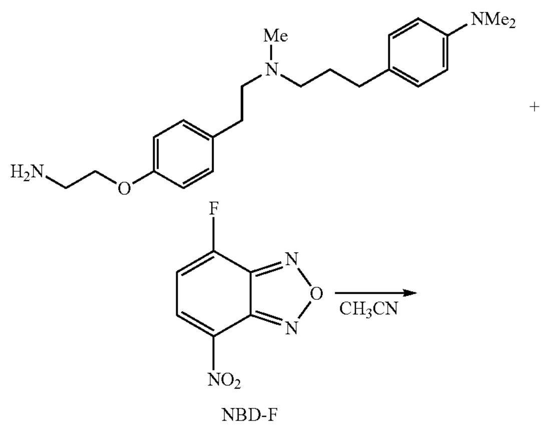

NBD-F

-continued

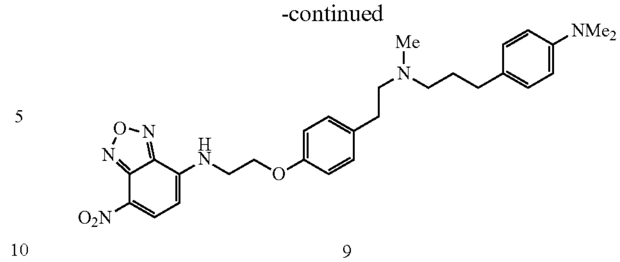

9

Compound 9

4-(3-{[4-(2-aminoethoxy)phenethyl](methyl)amino}propyl)-N,N-dimethylaniline (17.4 mg, 49 μmol) was dissolved in acetonitrile (500 μL), and subsequently, NBD-F (9.9 mg, 55 μmol) dissolved in acetonitrile (500 μL) was added to be reacted at room temperature for 1 hour. An aqueous solution of saturated sodium bicarbonate was added to the reaction solution, extraction was made with ethyl acetate, and the extract was dried with anhydrous sodium sulfate. The residue obtained by concentrating the extracted liquid under reduced pressure was purified with column chromatography (silica gel, acetone), and red brown oily Compound 9 (17.3 mg, 33 μmol, 67%) was yielded.

$^1H$ NMR (400 MHz, $CDCl_3$) δ: 1.69-1.8 (complex, 2H, $CH_2CH_2CH_2$), 2.16 (s, 3H, $NCH_3$), 2.25-2.44 (complex, 4H, $ArCH_2$ and $NCH_2$), 2.50 (t, J=7.8 Hz, 2H, $ArCH_2$), 2.67-2.74 (m, 2H), 2.89 (s, 6H, $N(CH_3)_2$), 3.85-3.91 (br m, 2H, $HNCH_2CH_2O$), 4.28 (t, J=5 Hz, 2H, $ArOCH_2$), 6.27 (d, J=8.5 Hz, 1H, ArH), 6.67 (d, J=8.7 Hz, 2H, ArH), 6.84 (d, J=8.7 Hz, 2H, ArH), 7.03 (d, J=8.7 Hz, 2H, ArH), 7.12 (d, J=8.7 Hz, 2H, ArH), 8.50 (d, J=8.5 Hz, 2H, ArH).

Synthesis of Compound 10

Example 10

Compound 10 was synthesized according to the procedure described below.

ATTO565 (NHS ester) Conjugation Kit was used for preparation from 5-(2-aminoethoxy)-N-(3-(4-(dimethylamino)phenyl)propyl)-N-methyl-2,3-dihydro-1H-inden-1-amine. In 0.1 mL of acetonitrile, 1 mg of ATTO565 (NHS ester) and 4-(3-{[4-(2-aminoethoxy)benzyl]methylamino}propyl)-N,N-dimethylaniline of the same mol as the ATTO565 (NHS ester) were mixed to be reacted for 16 hours. The reaction solution was concentrated under reduced pressure, the residue was purified with reverse phase PLC (ODS, water/acetonitrile=1/50), and a red brown solid of Compound 10 was yielded.

Synthesis of Compound 11

Example 11

Compound 11 was synthesized according to the procedure described below.

3-(4-methylphenyl) propan-1-amine was used to synthesize Compound 11 by the same scheme as the synthesis of Compound 1.

$^1H$ NMR (400 MHz, $CDCl_3$): δ: 1.75-1.85 (br, 2H, $ArCH_2CH_2$), 1.96-2.1 (m, 2H, $ArCH_2CH_2$), 2.16 (s, 3H, $NCH_3$), 2.30 (s, 3H, $ArCH_3$), 2.37-2.68 (complex, 4H, $NCH_2$ and $ArCH_2$), 2.71-2.93 (complex, 2H, $ArCH_2$), 3.86-3.93 (br, 2H, $HNCH_2$), 4.30 (t, J=5 Hz, 2H, $OCH_2$), 4.34-4.42 (br, 1H, ArCHN), 6.29 (d, J=8.7 Hz, 1H, ArH), 6.76 (s, 1H, ArH), 6.76-6.79 (m, 1H, ArH), 7.02-7.09 (complex, 5H, ArH), 8.51 (d, J=8.7 Hz, 1H, ArH).

Synthesis of Compound 12

Example 12

Compound 12 was synthesized according to the procedure described below.

3-(4-methoxyphenyl) propan-1-amine was used to synthesize Compound 12 by the same scheme as the synthesis of Compound 1.

$^1$H NMR (400 MHz, $CDCl_3$): δ: 1.7-1.9 (complex, 2H, $ArCH_2CH_2$), 2.0-2.1 (m, 2H, $ArCH_2CH_2$), 2.21 (s, 3H, $NCH_3$), 2.4-2.67 (complex, 4H, $NCH_2$ and $ArCH_2$), 2.73-2.94 (complex, 2H, $ArCH_2$), 3.77 (s, 3H, $OCH_3$), 3.88-3.93 (br, 2H, $HNCH_2$), 4.30 (t, J=5 Hz, 2H, $OCH_2$), 4.37-4.48 (m, 1H, ArCHN), 6.29 (d, J=8.7 Hz, 1H, ArH), 6.76 (s, 1H, ArH), 6.77-6.83 (m, 1H, ArH), 6.8 (d, J=8.5 Hz, 2H, ArH), 7.04-7.1 (complex, 1H, ArH), 7.07 (d, J=8.5 Hz, 2H, ArH), 8.51 (d, J=8.7 Hz, 1H, ArH).

Fluorescent Staining of Intracellular Vesicle by Using Compound 1 and Anti-CD63 Antibody Example 13

Fluorescent staining of intracellular vesicles was performed by using Compound 1 synthesized in Example 1 and the anti-CD63 antibody. The procedure is illustrated below.

(1) $3\times10^4$ of mouse malignant melanoma cells B16F10 (obtained from RIKEN Cell Bank) were plated in a glass bottom dish (Matsunami) and cultured for 24 hours. As the culture medium, a culture medium in which 1× penicillin-streptomaine (26252-94 (NACALAI TESQUE)) and 10% fetal bovine serum (Nichirei) were added to high glucose (D6046 (Merck)) in Dulbecco's Modified Eagle Medium (DMEM) was used. The culturing was performed under 5% $CO_2$ at 37° C.

(2) Compound 1 was added to the culture medium to have the final concentration of 0.3 μM.

(3) The culture medium was aspirated off after 5 minutes from the addition of Compound 1, 1 mL of 4% paraformaldehyde/phosphate buffer (09154-14 (NACALAI TESQUE)) was added, and the mixture was fixed at room temperature for 15 minutes.

(4) After the 4% paraformaldehyde/phosphate buffer was aspirated off, 1 mL of phosphate buffer was added.

(5) 1 μL of DAPI (Cellstain (registered trademark) DAPI solution (Dojindo Laboratories)) was added, and the mixture was allowed to stand for 15 minutes to perform fluorescent staining of the nuclei.

(6) The phosphate buffer was aspirated off, and operation of washing with the phosphate buffer was performed three times.

(7) After the washing, 1 mL of the reaction liquid of the anti-CD63 antibody (D263-3(MBL)) diluted at 1/1000 was added to the 10% Blocking One (NACALAI TESQUE)/phosphate buffer, and the mixture was allowed to stand at room temperature for 1 hour.

(8) The phosphate buffer was aspirated off, and operation of washing with the phosphate buffer was performed three times.

(9) After the washing, 1 mL of the reaction liquid of anti-mouse IgG H&L (Alexa Fluor 594) (ab150116 (Abcam)) diluted at 1/1000 was added to the 10% Blocking One/phosphate buffer, and the mixture was allowed to stand at room temperature for 1 hour.

(10) The phosphate buffer was aspirated off, and operation of washing with the phosphate buffer was performed four times.

(11) Measurement was performed by using a fluorescence microscope (BZ-9000 (Keyence)). Note that, in the measurement, Compound 1 was excited at 470 nm, and the antibody conjugated with CD63 was excited at 540 nm. Further, the DAPI was excited at 360 nm.

The result is illustrated in FIG. 1. FIG. 1A represents a fluorescence microscopic image of a whole cell. FIG. 1B represents an enlarged view of a part surrounded by the frame of FIG. 1A. Compound 1 emitted green fluorescence, and the antibody conjugated with CD63 emitted red fluorescence. It was indicated from FIG. 1 that fluorescence was emitted from Compound 1 and the antibody conjugated with CD63. Further, as seen from FIG. 1A and FIG. 1B, the fluorescence from Compound 1 and the fluorescence from the antibody conjugated with CD63 overlap each other. CD63 is a marker of cellular vesicles derived from endosomes. Therefore, it is indicated from the result of FIG. 1 that Compound 1 can fluorescently stain cellular vesicles.

Detection of Autophagosome by Compound 1

Example 14

An endosome-derived intracellular vesicle formation inhibitor (PIKfyve inhibitor) was used to detect autophagosomes. The procedure is illustrated below.

(1) $3\times10^4$ of B16F10 cells were plated in a glass bottom dish and cultured for 24 hours.

(2) Compound 1 was added to have the final concentration of 3 μM.

(3) Measurement was performed by using a fluorescence microscope. Note that the measurement was performed with excitation at 470 nm.

(4) PIKfyve inhibitor (HY-13228 (MedChemExpress)) was then added to the culture medium to have the final concentration of 10 μM, which was cultured for 1 hour.

(5) Measurement was performed by using the fluorescence microscope.

(6) PIKfyve inhibitor-containing culture medium was aspirated off, and washing operation was performed twice with a new culture medium, which was cultured with another new culture medium for 3 hours.

(7) Measurement was performed by using the fluorescence microscope.

The result is illustrated in FIG. 2. FIG. 2A represents a fluorescence microscopic image of observed fluorescence emitted from Compound 1 before the addition of the PIKfyve inhibitor. FIG. 2B represents a phase-contrast microscopic image before the addition of the PIKfyve inhibitor. FIG. 2C represents a fluorescence microscopic image of observed fluorescence emitted from Compound 1 after the addition of the PIKfyve inhibitor. FIG. 2D represents a phase-contrast microscopic image after the addition of the PIKfyve inhibitor. FIG. 2E represents a fluorescence microscopic image of observed fluorescence emitted from Compound 1 after the cells were cultured for 3 hours after the removal of the PIKfyve. FIG. 2F represents a phase-contrast microscopic image after the cells were cultured for 3 hours after the removal of the PIKfyve. It can be seen that cellular vesicles are present in the cell from FIG. 2A and that a melanosome is present in the cell from FIG. 2B. Reduction in the fluorescence intensity and corruption and foaming of the melanosome were found when the PIKfyve inhibitor was added, as illustrated in FIG. 2C and FIG. 2D. This showed that Compound 1 can also fluorescently stain the PIKfyve dependent cellular vesicles. Further, it can be seen from FIG. 2E and FIG. 2F that, in the cells after the removal of the PIKfyve inhibitor, the autophagosome membrane enclosing the melanosome was fluorescently stained by Compound 1. The autophagosome membrane is derived from endosomes. Therefore, it was indicated that Compound 1 can fluorescently stain cellular vesicles derived from endosomes even when the PIKfyve inhibitor is used.

Fluorescent Staining of Cellular Vesicle in Human Cell

It has been indicated from Example 13 and Example 14 that Compound 1 fluorescently stains of cellular vesicles derived from mice. Accordingly, fluorescent staining was also performed for cells derived from human.

Example 15

Compound 1 was used to fluorescently stain cellular vesicles of HEK293 cells. The procedure is illustrated below.

(1) HEK293A cells (ThermoFisher) were plated in a glass bottom dish and cultured for 24 hours. As the culture medium, a culture medium in which 10% FCS and 1× penicillin-streptomaine were added to DMEM Low Glucose (D6046 (Merck)) was used.

(2) Compound 1 was added to have the final concentration of 0.3 μM.

(3) Measurement was performed by using the fluorescence microscope. Note that the measurement was performed with excitation at 470 nm.

Example 16

Compound 1 was used to fluorescently stain cellular vesicles of keratinocyte cells (PSVK1). The procedure is illustrated below.

(1) PSVK1 cells (obtained from National Institute of Biomedical Innovation, Health and Nutrition, Cell Bank) were plated in a glass bottom dish and cultured for 24 hours. Keratinocyte Growth Medium 2 Kit (C-20111 (TAKARA BIO)) was used as the culture medium.

(2) Compound 1 was added to have the final concentration of 0.3 μM.

(3) Measurement was performed by using the fluorescence microscope. Note that the measurement was performed with excitation at 470 nm.

Figure 3B:
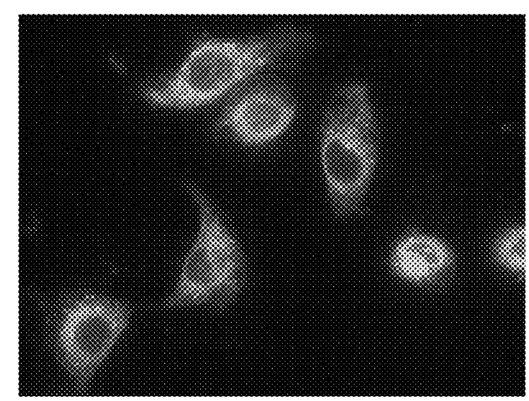
Figure 4A:
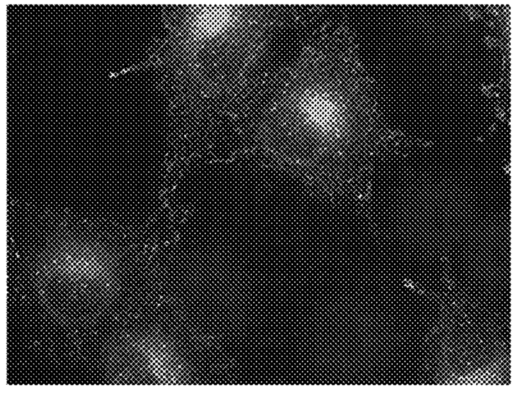
FIGS. 4A-4D represent photographs as substitutes for drawings illustrating a result of Example 17.
Figure 4C:
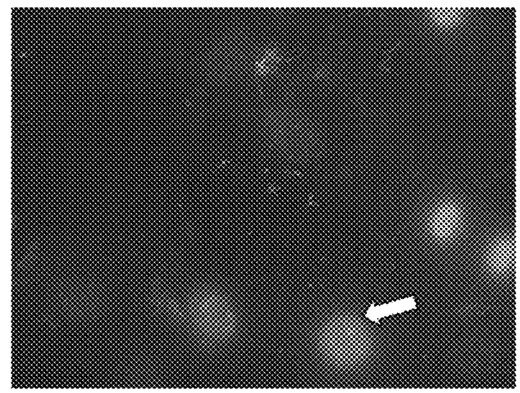
Figure 4B:
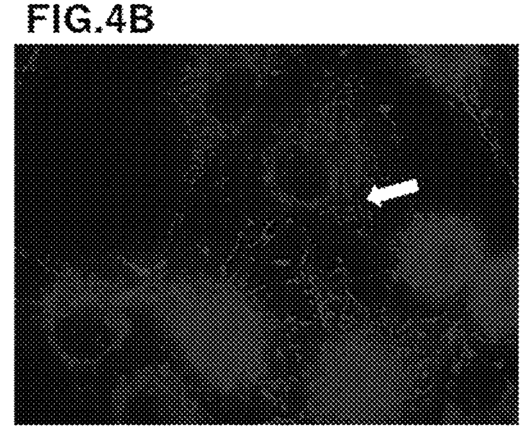
Figure 4D:
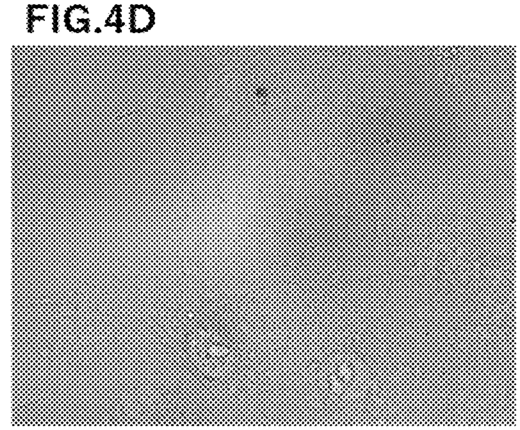

The result is illustrated in FIG. 3. FIG. 3A represents a fluorescence microscopic image of Example 15. FIG. 3B represents a fluorescence microscopic image of Example 16. It was indicated from FIG. 3A and FIG. 3B that Compound 1 can fluorescently stain the cellular vesicle of the HEK293 cell and the cellular vesicle of the PSVK1 cell that are human cells.

Specificity 1 of Compound 1 to Cellular Vesicle

Example 17

Fluorescent staining was performed on cellular vesicles of living cells by using Compound 1. The procedure is illustrated below.

(1) $3\times10^4$ of B16F10 cells were plated in a collagen coated glass bottom dish (Matsunami) and cultured for 24 hours.

(2) A mitochondrial staining reagent (MitoTracker Red (ThermoFisher)) was added to the culture medium to have the final concentration of 1 μM to fluorescently stain mitochondria.

(3) The culture medium was aspirated off after 5 minutes, 4% paraformaldehyde/phosphate buffer was added, and the mixture was fixed at room temperature for 15 minutes.

(4) The 4% paraformaldehyde/phosphate buffer was aspirated off, and 1 mL of phosphate buffer was added.

(5) 1 μL of DAPI was added and allowed to stand for 15 minutes to fluorescently stain the nuclei.

(6) The phosphate buffer was aspirated off, and operation of washing with a phosphate buffer was performed five times.

(7) After the washing, 2 mL of DMEM culture medium was added.

(8) Another $3\times10^4$ of B16F10 cells were plated and cultured for 24 hours.

(9) Compound 1 was added to have the final concentration of 0.3 μM.

(10) Measurement was performed by using the fluorescence microscope. Note that, in the measurement, Compound 1 was excited at 470 nm, the mitochondrial staining reagent was excited at 540 nm, and the DAPI was excited at 360 nm.

The result is illustrated in FIG. 4. FIG. 4A represents a fluorescence microscopic image of observed fluorescence emitted from Compound 1. FIG. 4B represents a fluorescence microscopic image of observed fluorescence emitted from the mitochondrial staining reagent. FIG. 4C represents a fluorescence microscopic image of observed fluorescence emitted from the DAPI staining the nuclei. FIG. 4D represents a phase-contrast microscopic image. While the cells were present in the whole microscopic image as seen from FIG. 4D, cellular vesicles of only some of the cells were fluorescently stained as seen in FIG. 4A. As indicated by arrows in FIG. 4B and FIG. 4C, cells whose cellular vesicles were not fluorescently stained by Compound 1 in FIG. 4A were dead cells. Therefore, it was indicated that Compound 1 fluorescently stains cellular vesicles of living cells.

Specificity 2 of Compound 1 to Cellular Vesicle

Cellular vesicles were fluorescently stained by Compound 1 and other cellular vesicle staining agents, and comparison was made.

Example 18

Compound 1 was used for fluorescent staining of intracellular vesicles. The procedure is illustrated below.

(1) $3\times10^4$ of B16F10 cells were plated in a glass bottom dish and cultured for 24 hours.

(2) Compound 1 was added to the culture medium to have the final concentration of 3 μM.

(3) Measurement was performed by using the fluorescence microscope. Note that the measurement was performed with excitation at 470 nm.

Comparative Example 1

Comparative example 1 is the same as Example 18 except that, instead of Compound 1, 1 μL/mL of ExoSparkler Mem Dye-Red (340-09671 (Dojindo Laboratories)) was added to the culture medium, the culture medium was aspirated off after the addition of ExoSparkler Mem Dye-Red, and a new culture medium was added for washing. Note that the measurement was performed with excitation at 540 nm.

Figure 5A:
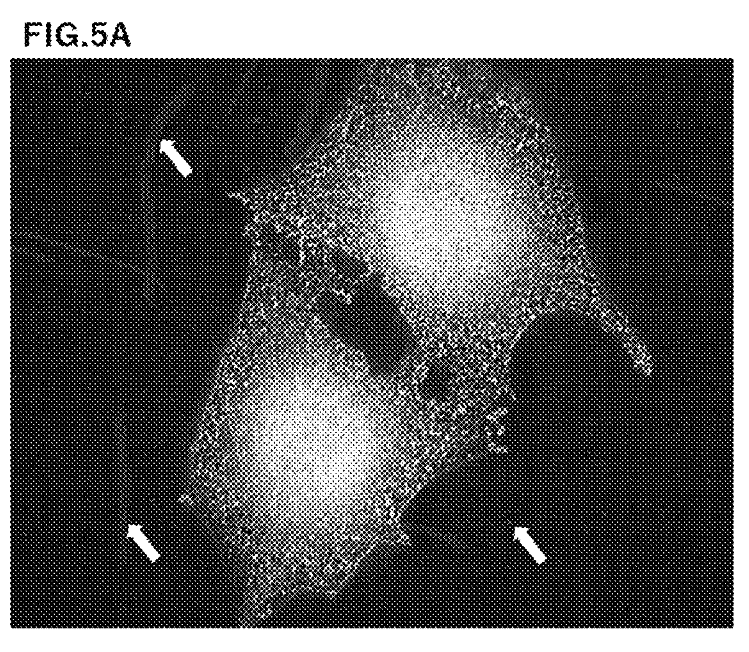
FIGS. 5A-5C represent photographs as substitutes for drawings illustrating an example indicating that Compound 1 has high specificity to cellular vesicles.
Figure 5B:
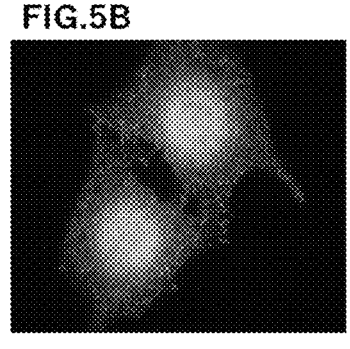
Figure 5C:
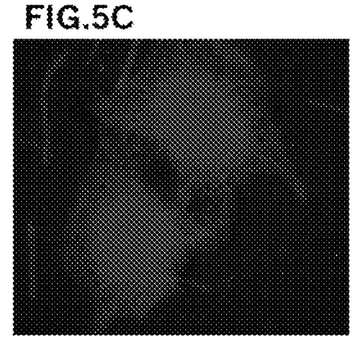
Figure 6A:
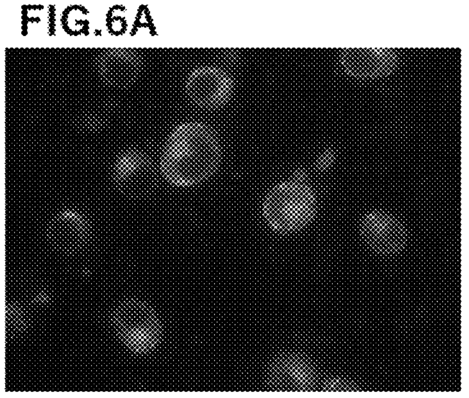
FIGS. 6A-6D represent photographs as substitutes for drawings illustrating another example indicating that Compound 1 has high specificity to cellular vesicles.
Figure 6C:
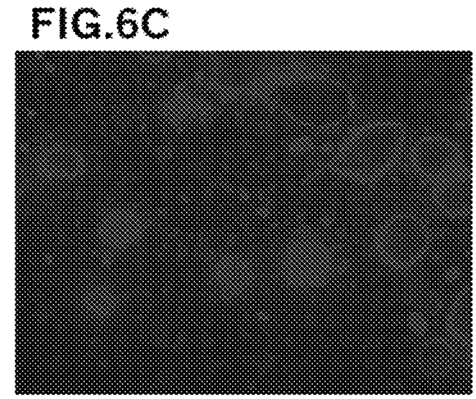
Figure 6B:
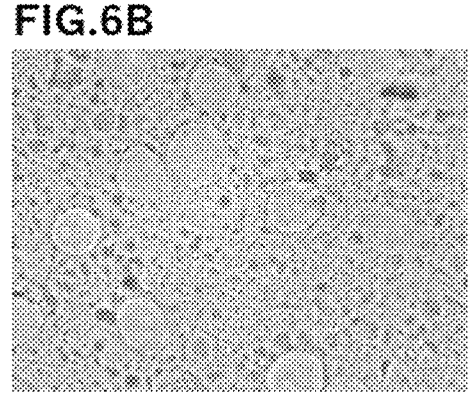
Figure 6D:
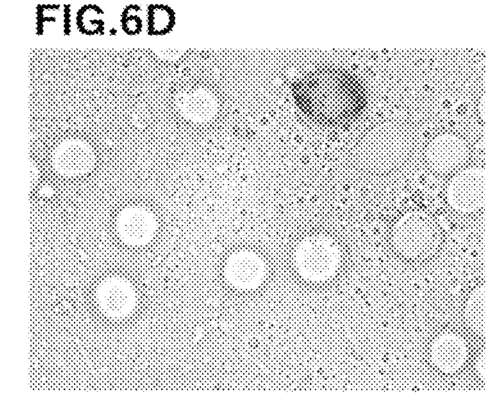

The result is illustrated in FIG. 5. FIG. 5A represents overlapped fluorescence microscopic images of Example 18 and Comparative example 1. FIG. 5B represents a fluorescence microscopic image of Example 18. FIG. 5C represents a fluorescence microscopic image of Comparative example 1. It was indicated from FIG. 5 that cellular vesicles were fluorescently stained in Example 18 and Comparative example 1. However, while only the cellular vesicles were fluorescently stained in Example 18 as seen from FIG. 5A and FIG. 5B, debris or the like other than cellular vesicles were fluorescently stained in Comparative example 1 despite the fact that washing was performed after staining, as indicated by the arrow in FIG. 5A. Therefore, it was indicated that Compound 1 has high specificity to cellular vesicles.

Specificity 3 of Compound 1 to Cellular Vesicle

Cellular vesicles were fluorescently stained by Compound 1 and other cellular vesicle staining agents in the presence of foreign substances, and comparison was made.

Example 19

Intracellular vesicles were fluorescently stained by Compound 1 in the presence of foreign substances. The procedure is illustrated below.

(1) 100 mg of mouse dung was collected, and the collected dung was suspended in 10-fold volume (1 mL) of phosphate buffer.

(2) B16F10 cells were detached using trypsin EDTA (NACALAI TESQUE) and collected, and $1\times10^4$ cells were suspended in 100 μL of phosphate buffer and mixed with 10 μL of the mouse dung suspension of (1).

(3) The suspension of the cells and the drug was spread on a glass bottom dish, and 300 μM of Compound 1 was added to have the final concentration of 0.3 μM.

(4) Measurement was performed by using the fluorescence microscope. Note that the measurement was performed with excitation at 470 nm.

Comparative Example 2

Comparative example 2 is the same as Example 19 except that, instead of Compound 1, 1 μL of CellMask reagent (C10045 (ThermoFisher)) was added to the suspension of the cells and the dung. Note that the measurement was performed with excitation at 540 nm.

The result is illustrated in FIG. 6. FIG. 6A represents a fluorescence microscopic image of Example 19. FIG. 6B represents a phase-contrast microscopic image of Example 19. FIG. 6C represents a fluorescence microscopic image of Comparative example 2. FIG. 6D represents a phase-contrast microscopic image of Comparative example 2. It was indicated from FIG. 6A and FIG. 6B that only the cellular vesicles were fluorescently stained in Example 19 even in the presence of foreign substances. Further, as seen from FIG. 6C and FIG. 6D, not only the cellular vesicles but also the foreign substances were fluorescently stained in Comparative example 2. It was indicated that, while a large amount of living intestinal bacteria and food digestate are included in mouse dung, Compound 1 does not react with such intestinal bacteria and food digestate and can specifically fluorescently stain cellular vesicles.

Fluorescent Staining of Exosome

Example 20

Fluorescent staining of exosomes that are extracellular vesicles was performed. The procedure is illustrated below.

(1) Compound 1 dissolved in DMSO was dissolved in a phosphate buffer to have the final concentration of 0.3 μM.

(2) 10 ng of milk exosomes were added to the phosphate buffer with Compound 1 dissolved therein.

(3) Measurement was performed by using an image analysis device ChemiDoc (Bio-Rad). Note that the measurement was performed with excitation at 302 nm.

Comparative Example 3

Comparative example 3 is the same as Example 20 except that the milk exosome was not added.

Figure 7:
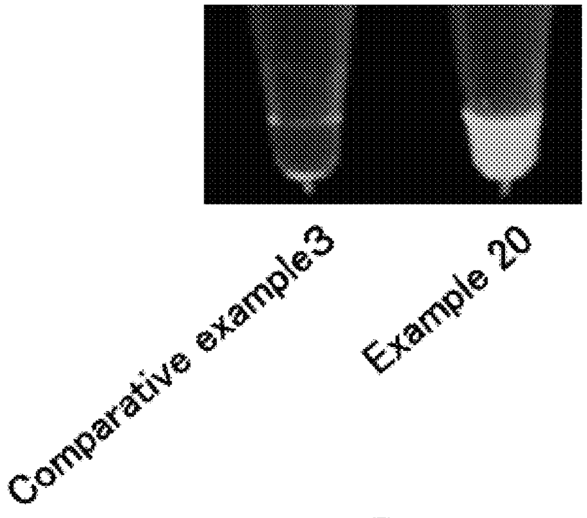
FIG. 7 is a photograph substitute for a drawing illustrating a result of fluorescent staining of exosomes.

The result is illustrated in FIG. 7. As illustrated in FIG. 7, in Example 20 with milk exosomes added, fluorescence was emitted. In contrast, in Comparative example 3, no fluorescence was emitted. Therefore, it was indicated that Compound 1 conjugates with exosomes that are cellular vesicles and emits fluorescence.

Creation of Calibration Curve in Exosome Detection

Example 21

A calibration curve in exosome detection was created. The procedure is illustrated below.

(1) A solution obtained by mixing 50 μL of fetal bovine serum and 50 μL of phosphate buffer was put in wells of a 96-well microplate for fluorescence (3-3321-03 (AS ONE)).

(2) Milk exosomes were added to each well within a range of 0.1 to 1 ng.

(3) Autofluorescence (excitation at 488 nm) was measured with a fluorescence plate reader (GroMax Multi (Promega)).

(4) Compound 1 was added to each well to have the final concentration of 0.3 μM, and fluorescence was measured (excitation at 488 nm). In this measurement, a value obtained by subtracting the autofluorescence intensity from the resulted fluorescence intensity was used as a measured value.

Figure 8:
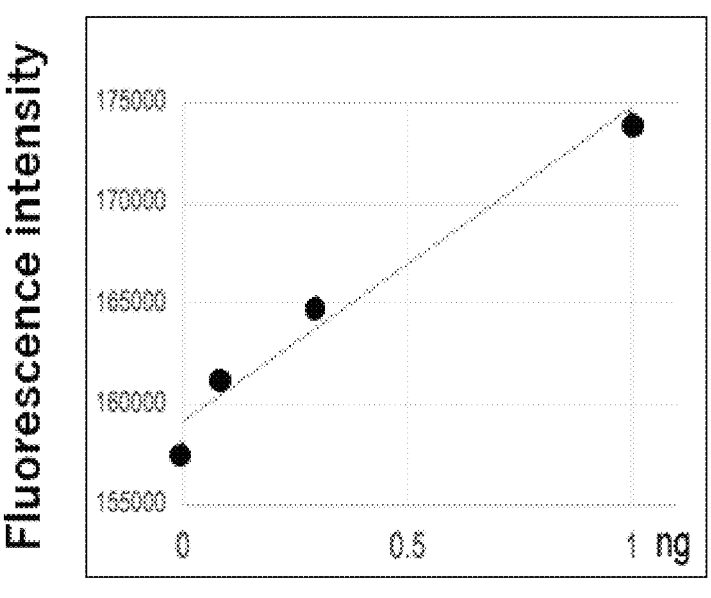
FIG. 8 is a diagram illustrating a calibration curve in exosome detection.

The fluorescence intensity was measured at each exosome concentration, and a calibration curve created from the result is illustrated in FIG. 8. It was indicated that, while exosomes were also contained in fetal bovine serum, the fluorescence intensity increased depending on the amount of externally added milk exosomes. It is therefore possible to detect 1 ng of exosomes from the calibration curve of FIG. 8 even in the presence of foreign substances.

Measurement of Exosome in Food

The calibration curve obtained in Example 21 was used to measure exosomes in foods.

Example 22

Exosomes contained in black coffee were measured. The procedure is illustrated below.

(1) A solution obtained by mixing 50 μL of black coffee (UCC) and 50 μL of phosphate buffer was put in wells of a 96-well microplate for fluorescence.

(2) Autofluorescence (excitation at 488 nm) was measured with the fluorescence plate reader.

(4) Compound 1 was added to the wells to have the final concentration of 0.3 μM, and fluorescence was measured (excitation at 488 nm). In this measurement, a value obtained by subtracting the autofluorescence intensity from the resulted fluorescence intensity was used as a measured value.

Example 23

Example 23 is the same as Example 22 except that, instead of black coffee, coffee with milk (Asahi) was used.

Example 24

Example 24 is the same as Example 22 except that, instead of black coffee, lactic acid bacteria drink (Yakult) was used.

Example 25

Example 25 is the same as Example 22 except that, instead of black coffee, 1% skim milk (Fuji Film Wako) was used.

Example 26

Example 26 is the same as Example 22 except that, instead of black coffee, milk (Meiji) was used.

Example 27

Example 27 is the same as Example 22 except that, instead of black coffee, vegetable juice (Kagome) was used.

The result is illustrated in FIG. 9. It was indicated from FIG. 9 that exosomes in foods can be measured. No exosome was detected from the black coffee. Further, it was indicated that exosomes were also contained in the vegetable juice.

Incorporation of Labeled Exosome into Cell by Compound 1 and Exosome Staining Reagent Example 28

Incorporation of fluorescently stained labeled exosomes into cells by using Compound 1 and an exosome staining reagent was measured. The procedure is illustrated below.

(1) Milk exosomes (EXO-AB-01 (COSMO BIO)) were stained for 5 minutes with Compound 1 (final concentration of 0.3 μM) and ExoSparkler Mem Dye-Red (340-09671 (Dojindo Laboratories)) (1 μL) and then purified with a column attached to ExoSparkler Mem Dye-Red to create labeled milk exosomes.

(2) HEK293A cells were cultured, and the labeled milk exosomes were added.

(3) After 12 hours from the addition of the labeled milk exosomes, measurement was performed by using a fluorescence microscope. Note that, in the measurement, Compound 1 was excited at 470 nm, and ExoSparkler Mem Dye-Red was excited at 540 nm.

The result is illustrated in FIG. 10. FIG. 10A represents overlapped fluorescence microscopic images of the fluorescence emitted from both Compound 1 and ExoSparkler Mem Dye-Red. FIG. 10B represents a fluorescence microscopic image of observed fluorescence emitted from Compound 1. FIG. 10C represents a fluorescence microscopic image of observed fluorescence emitted from ExoSparkler Mem Dye-Red. ExoSparkler Mem Dye-Red is a fluorescence reagent conjugating with exosomes. It was indicated from FIG. 10A that, since the fluorescence of Compound 1 and the fluorescence of ExoSparkler Mem Dye-Red overlap, Compound 1 also specifically conjugates with the exosomes. Further, it was indicated that exosomes labeled with Compound 1 are incorporated into cells.

Inhibition of Incorporation of Labeled Melanosome into Cell

Example 29

Incorporation of melanosomes into cells was measured in the presence of a melanosome uptake inhibitor. The procedure is illustrated below.

(1) B16F10 cells were cultured in 10 mL of culture medium.

(2) Forskolin (F0855 (Tokyo Chemical Industry)) was added to the culture medium to have the final concentration of 20 μM, which was cultured for 48 hours to induce melanin synthesis.

(3) After the culture medium was aspirated off, the culture medium was replaced with flesh Forskolin containing culture medium, which was cultured for another 24 hours.

(4) The culture medium was collected in a 15 mL centrifugal tube, which was centrifuged at 3000 rpm for 5 minutes, mixed cells were precipitated and removed, and supernatant was collected.

(5) The collected supernatant was transferred to another 15 mL centrifugal tube, which was centrifuged at 8000 rpm for 10 minutes.

(6) The precipitate was suspended in 1 mL of phosphate buffer and transferred to a 2 mL centrifugal tube.

(7) Centrifugation was performed at 12000 rpm for 5 minutes, the supernatant was discarded, and the precipitate was further washed twice with 1 mL of phosphate buffer.

(8) The precipitate resulted after washing was suspended in 100 μL of phosphate buffer, Compound 1 was added to have the final concentration of 3 μM, and staining was performed for 5 minutes.

(9) Centrifugation was performed at 12000 rpm for 5 minutes, the supernatant was discarded, and the precipitate was washed twice with 1 mL of phosphate buffer.

(10) The precipitate resulted after washing was suspended in 100 μL of phosphate buffer to create labeled melanocytes.

(11) $5\times10^4$ of keratinocyte cells were plated in wells of a 96-well microplate.

(12) The labeled melanocyte (10 μL) and the melanosome uptake inhibitor (final concentration of 10 μM) were added to the wells. As the melanosome uptake inhibitor, 6-shogaol (192-16161 (Fujifilm Wako)) was used.

(13) After 12 hours, the cells were washed twice with 100 μL of phosphate buffer.

(14) A plate reader (GroMax Multi (Promega)) was used to measure the labeled melanosomes. Note that the measurement was performed with excitation at 488 nm.

Comparative Example 4

Comparative Example 4 is the same as Example 29 except that the measurement with the plate reader was performed for absorbance at 450 nm.

Figure 11A:
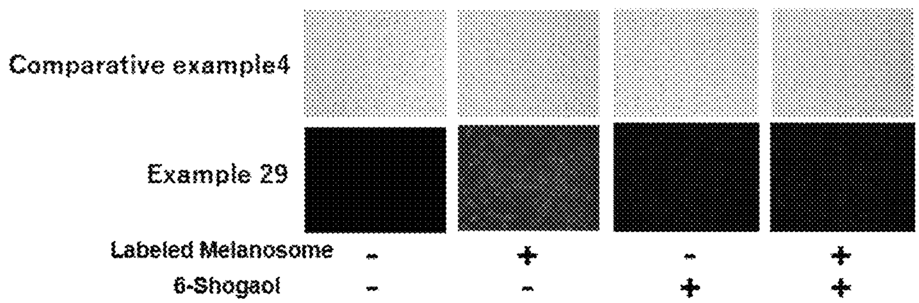
FIGS. 11A-11C represent diagrams illustrating a result of cell incorporation inhibition of labeled melanosomes.
Figure 11B:
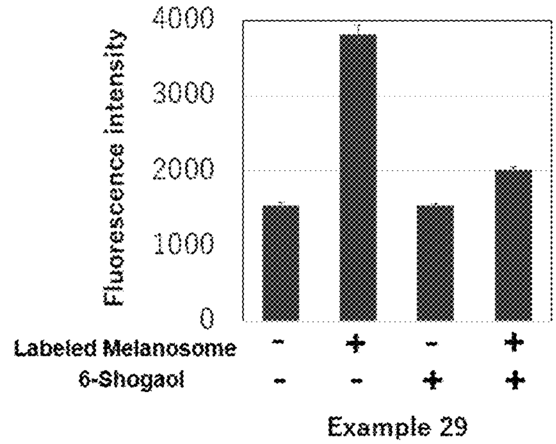
Figure 11C:
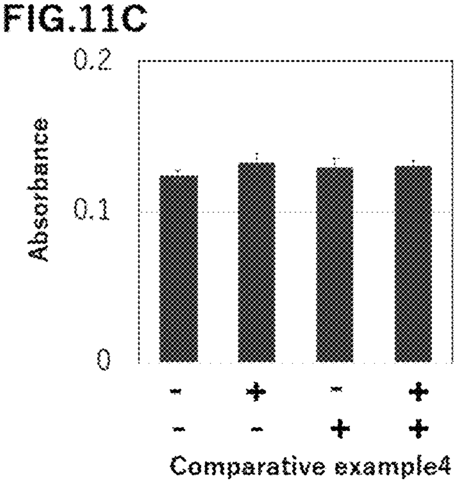

The result is illustrated in FIG. 11. FIG. 11A represents a fluorescence microscopic image of Example 29 and a phase-contrast microscopic image of Comparative example 4. FIG. 11B illustrates the result of Example 29. FIG. 11C illustrates the result of Comparative example 4. It was indicated from FIG. 11A and FIG. 11B that, while the labeled melanosomes are incorporated in keratinocyte cells in the absence of the melanosome uptake inhibitor, incorporation of the labeled melanosomes into keratinocyte cells is inhibited in the presence of the melanosome uptake inhibitor because of a reduced fluorescence intensity. In contrast, incorporation of melanosomes into keratinocytes were unable to be evaluated in the absorbance measurement in Comparative example 4. Therefore, it was indicated that the use of Compound 1 enables evaluation of incorporation of melanosomes into keratinocytes due to a melanosome uptake inhibitor.

Fluorescent Staining of Cellular Vesicles with Compound 2 to Compound 4 and Compound 6 to Compound 12

Example 30

Example 30 is the same as Example 14 without the PIKfyve inhibitor addition except that Compound 2 was used instead of Compound 1.

Example 31

Example 31 is the same as Example 14 without the PIKfyve inhibitor addition except that Compound 3 was used instead of Compound 1.

Example 32

Example 32 is the same as Example 14 without the PIKfyve inhibitor addition that Compound 4 was used instead of Compound 1.

Example 33

Example 33 is the same as Example 14 without the PIKfyve inhibitor addition except that Compound 6 was used instead of Compound 1.

Example 34

Example 34 is the same as Example 14 without the PIKfyve inhibitor addition except that Compound 7 was used instead of Compound 1.

Example 35

Example 35 is the same as Example 14 without the PIKfyve inhibitor addition except that Compound 8 was used instead of Compound 1.

Example 36

Example 36 is the same as Example 14 without the PIKfyve inhibitor addition except that Compound 9 was used instead of Compound 1.

Example 37

Example 37 is the same as Example 14 without the PIKfyve inhibitor addition except that Compound 10 was used instead of Compound 1 and that the excitation light was at 540 nm in the measurement.

Example 38

Example 38 is the same as Example 14 without the PIKfyve inhibitor addition except that Compound 11 was used instead of Compound 1.

Example 39

Example 39 is the same as Example 14 without the PIKfyve inhibitor addition except that Compound 12 was used instead of Compound 1.

Figures 12A, 12B, 12C, 12D, 12E, 12F, 12G, 12H, 12I, 12J, 12K:
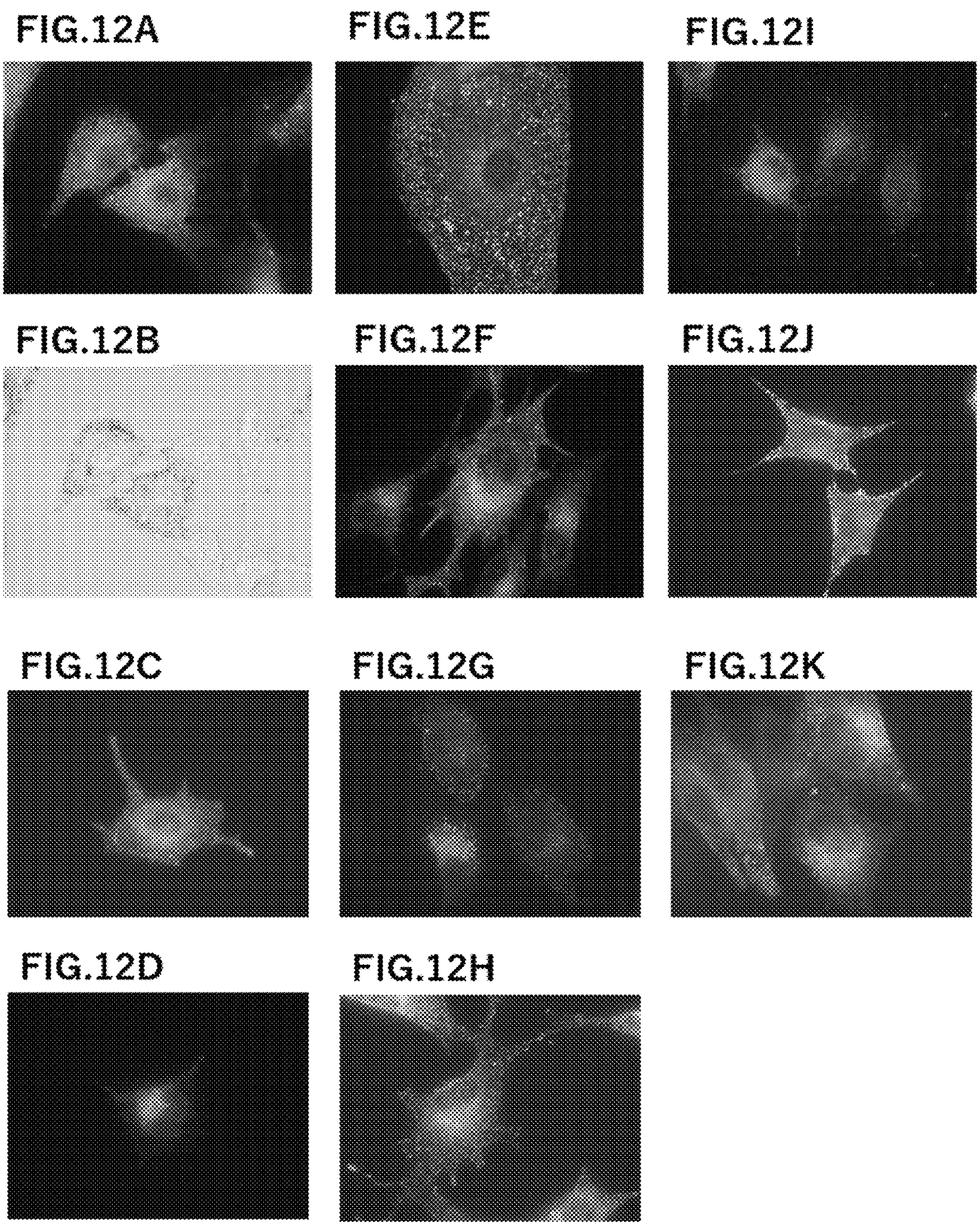
FIGS. 12A-12K represent photographs as substitutes for drawings illustrating a result of fluorescent staining of cellular vesicles.

The result is illustrated in FIG. 12. FIG. 12A is a fluorescence microscopic image of Example 30. FIG. 12B is a phase-contrast microscopic image of Example 30. FIG. 12C is a fluorescence microscopic image of Example 31. FIG. 12D is a fluorescence microscopic image of Example 32. FIG. 12E is a fluorescence microscopic image of Example 33. FIG. 12F is a fluorescence microscopic image of Example 34. FIG. 12G is a fluorescence microscopic image of Example 35. FIG. 12H is a fluorescence microscopic image of Example 36. FIG. 12I is a fluorescence microscopic image of Example 37. FIG. 12J is a fluorescence microscopic image of Example 38. FIG. 12K is a fluorescence microscopic image of Example 39. It was indicated from FIG. 12A and FIG. 12C to FIG. 12K that Compound 2 to Compound 4 and Compound 6 to Compound 12 can fluorescently stain cellular vesicles in the same manner as Compound 1. Further, it is possible to determine correlation between the fluorescence intensity and the melanin amount by measuring the fluorescence intensity of FIG. 12A and the melanin amount in the cell of FIG. 12B. Thus, it was suggested that it is possible to perform quality evaluation of the cell.

Fluorescence Intensity Measurement on Living Cell and Dead Cell

For each compound of Compound 1 to Compound 7, fluorescence intensity on living cells and dead cells was measured. The procedure is illustrated below.

Example 40

(1) B16F10 cells were detached using trypsin-EDTA and suspended in a phosphate buffer. In this step, 30% ethanol was added for making dead cells.
(2) The living cell suspension and the dead cell suspension were centrifuged at 2000 rpm for 3 minutes, respectively, to sediment cells.
(3) Washing with a phosphate buffer was performed twice, and the cells were counted. At this point of time, the viability of the living cells obtained from the living cell suspension was 70%.
(4) Compound 1 was added to $5\times10^4$ cells/100 μL to have the final concentration of 1 μM, and the fluorescence (excitation at 488 nm) was measured. In this step, a value obtained by dividing subtraction of the autofluorescence intensity from the resulted fluorescence intensity by the fluorescence intensity of only the phosphate buffer was used as a measured value.

Example 41

Example 41 is the same as Example 40 except that Compound 2 is used instead of Compound 1.

Example 42

Example 42 is the same as Example 40 except that Compound 3 is used instead of Compound 1.

Example 43

Example 43 is the same as Example 40 except that Compound 4 is used instead of Compound 1.

Example 44

Example 44 is the same as Example 40 except that Compound 5 is used instead of Compound 1.

Example 45

Example 45 is the same as Example 40 except that Compound 6 is used instead of Compound 1.

Example 46

Example 46 is the same as Example 40 except that Compound 7 is used instead of Compound 1.

Comparative Example 5

Comparative example 5 is the same as Example 40 except that a fluorescent compound expressed by the following formula is used instead of Compound 1.

[Formula 26]

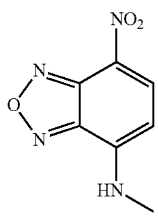

Figure 13:
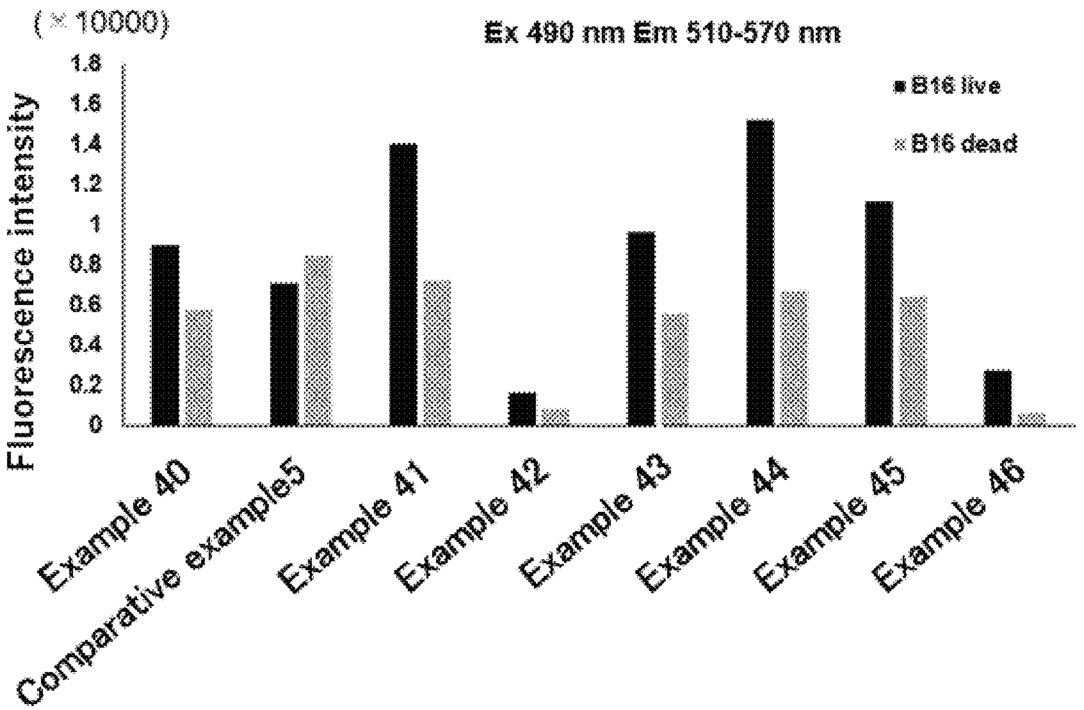
FIG. 13 is a diagram illustrating a result of fluorescence intensity measurement on living cells and dead cells by using Compound 1 to Compound 7.

The result is illustrated in FIG. 13. As seen from FIG. 13, in all of Example 40 to Example 46, the fluorescence intensity was higher in the living cells with a large difference from the fluorescence intensity of the dead cells. In contrast, in Comparative example 5, the difference between the fluorescence intensity of the living cells and the fluorescence intensity of the deal cells was small. Therefore, it was indicated that Compound 1 to Compound 7 have specificity to cellular vesicles of living cells.

Measurement of Exosomes in Serum of Tumor Transplanted Mouse

Example 47

Serum was collected from mice transplanted with melanoma cells, and exosomes in the serum were measured. The procedure is illustrated below.

(1) $5\times10^4$ of B16F10 cells were transplanted subcutaneously into mice (C57BL/6 (8W male)), and the tumor weight was measured after two weeks.

(2) Serum of the mice was collected, and 20 μL of the serum and 80 μL of phosphate buffer were mixed.

(3) Compound 1 was added to the mixed solution of the serum and the phosphate buffer to have the final concentration of 0.3 μM.

(4) After 15 minutes from the addition of Compound 1, measurement was performed with a fluorescence microscope. Note that the measurement was performed with excitation at 488 nm.

Figure 14:
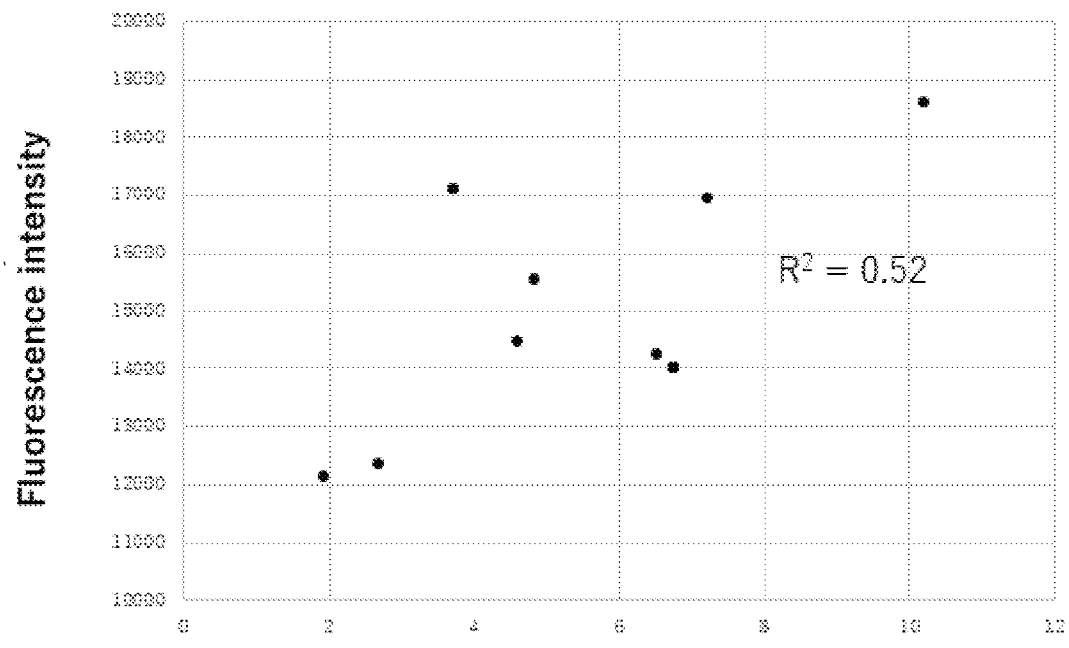
FIG. 14 is a diagram illustrating a result of Example 47.

The result is illustrated in FIG. 14. As seen from FIG. 14, the fluorescence intensity increased as the tumor weight increased. This indicated that exosomes in serum increase in accordance with an increase in tumor weight.

It was indicated from the above Examples that the compounds disclosed in the present application have high specificity to cellular vesicles and the compounds not reacted with cellular vesicles emit no fluorescence. It was therefore indicated that there is no need for operation of removing unreacted compounds after labeling, and sample loss can be suppressed.

INDUSTRIAL APPLICABILITY

The present disclosure is useful in the field where fluorescent staining of cellular vesicles is performed.

The invention claimed is:

1. A compound expressed by following Formula (1):

[Formula 1]

(1)

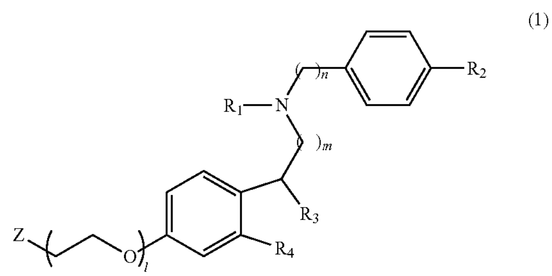

wherein in Formula (1), R1 represents H, a C1-C6 alkyl group, a hydroxy group, an amino group, or a carboxy group, R2 represents H, a C1-C18 alkyl group, a C1-C18 alkoxy group, a halogen element, $NO_2$ or N(CH3)2, and R3 and R4 each independently represent H or CH3, where R3 and R4 may be bonded to each other to form a ring and, when R3 and R4 are bonded to each other to form a ring, R3 and R4 are CH2, and wherein 1 represents 1 or 2, m represents 0 or 1, n represents 1, 2, or 3, and Z represents a fluorescent group.

2. The compound according to claim 1, wherein the compound expressed by Formula (1) is a compound expressed by following Formula (2):

[Formula 2]

(2)

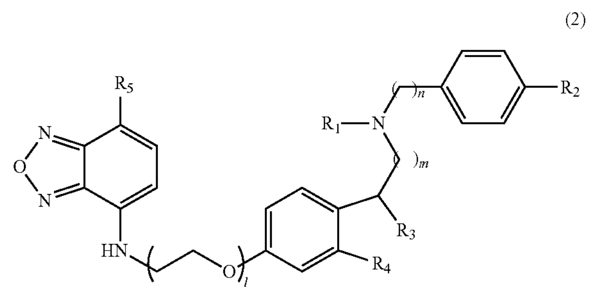

wherein in Formula (2), R1 represents H or CH3, R2 represents H, CH3, OCH3, or N(CH3)2, R3 and R4 each independently represent H or CH3, where R3 and R4 may be bonded to each other to form a ring and, when R3 and R4 are bonded to each other to form a ring, R3 and R4 are CH2, and R5 represents NO2, SO2NH2, or SO2N(CH3)2, and wherein 1 represents 1 or 2, m represents 0 or 1, and n represents 1, 2, or 3.

3. The compound according to claim 1, wherein the compound expressed by Formula (1) is a compound expressed by following Formula (3):

[Formula 3]

(3)

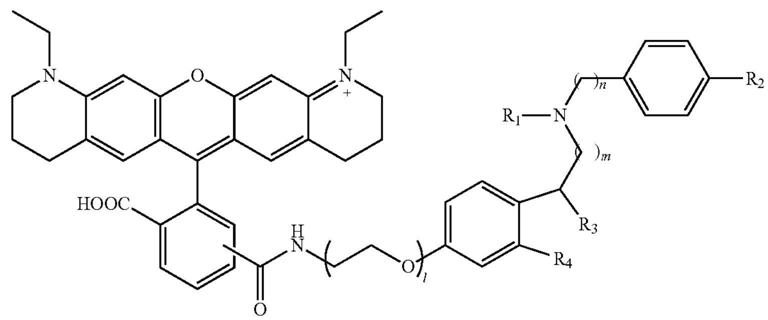

wherein in Formula (3), R1 represents H or CH3, R2 represents H, CH3, OCH3, or N(CH3)2, and R3 and R4 each independently represent H or CH3, where R3 and R4 may be bonded to each other to form a ring, and when R3 and R4 are bonded to each other to form a ring, R3 and R4 are CH2, and wherein 1 represents 1 or 2, m represents 0 or 1, and n represents 1, 2, or 3.

4. A cellular vesicle staining agent comprising the compound according to claim 1.

5. The cellular vesicle staining agent according to claim 4 further comprising another fluorescent compound.

6. A method of fluorescent staining for cellular vesicles, the method comprising:

a staining step of staining cellular vesicles by using the compound according to claim 1; and a detection step of detecting stained cellular vesicles in a sample.

7. The method of fluorescent staining for cellular vesicles according to claim 6 further comprising an evaluation step of evaluating the sample after the detection step.

8. The method of fluorescent staining for cellular vesicles according to claim 7, wherein the sample includes cosmetics, and wherein the method measures the cellular vesicles incorporated in cells to evaluate the cosmetics.

9. The method of fluorescent staining for cellular vesicles according to claim 7, wherein the sample includes pharmaceutical products, and wherein the method measures the cellular vesicles incorporated in cells to evaluate the pharmaceutical product.

10. The method of fluorescent staining for cellular vesicles according to claim 7, wherein the sample includes cells, and wherein the method measures the cellular vesicles in the cells to evaluate differentiation and quality of the cells.

11. The method of fluorescent staining for cellular vesicles according to claim 7, wherein the sample includes foods, and wherein the method measures the cellular vesicles in the foods to evaluate the foods.

12. The method of fluorescent staining for cellular vesicles according to claim 7, wherein the sample includes tissues collected from organisms, and wherein the method measures the cellular vesicles in the collected tissues to evaluate the tissues.

13. A cellular vesicle staining agent comprising the compound according to claim 2.

14. A cellular vesicle staining agent comprising the compound according to claim 3.

15. A method of fluorescent staining for cellular vesicles, the method comprising:

a staining step of staining cellular vesicles by using the compound according to claim 2; and a detection step of detecting stained cellular vesicles in a sample.

16. A method of fluorescent staining for cellular vesicles, the method comprising:

a staining step of staining cellular vesicles by using the compound according to claim 3; and a detection step of detecting stained cellular vesicles in a sample.

17. A method of fluorescent staining for cellular vesicles, the method comprising:

a staining step of staining cellular vesicles by using the cellular vesicle staining agent according to claim 4; and a detection step of detecting stained cellular vesicles in a sample.

18. A method of fluorescent staining for cellular vesicles, the method comprising:

a staining step of staining cellular vesicles by using the cellular vesicle staining agent according to claim 5; and a detection step of detecting stained cellular vesicles in a sample.

19. A method of fluorescent staining for cellular vesicles, the method comprising:

a staining step of staining cellular vesicles by using the cellular vesicle staining agent according to claim 13; and a detection step of detecting stained cellular vesicles in a sample.

20. A method of fluorescent staining for cellular vesicles, the method comprising:

a staining step of staining cellular vesicles by using the cellular vesicle staining agent according to claim 14; and a detection step of detecting stained cellular vesicles in a sample.

* * * * *